(12) United States Patent
Levendowski et al.

(10) Patent No.: US 6,625,485 B2
(45) Date of Patent: *Sep. 23, 2003

(54) METHOD FOR THE QUANTIFICATION OF HUMAN ALERTNESS

(75) Inventors: Daniel J. Levendowski, Carlsbad, CA (US); Zoran R. Konstantinovic, Vista, CA (US); Richard Olmstead, Van Nuys, CA (US); Christine Berka, Carlsbad, CA (US)

(73) Assignee: Advanced Brain Monitoring, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/172,060

(22) Filed: Jun. 14, 2002

(65) Prior Publication Data

US 2002/0183644 A1 Dec. 5, 2002

Related U.S. Application Data

(62) Division of application No. 09/345,046, filed on Jun. 30, 1999, now Pat. No. 6,496,724.
(60) Provisional application No. 60/114,528, filed on Dec. 31, 1998.

(51) Int. Cl.$^7$ .............................. A61B 5/00; G08B 23/00

(52) U.S. Cl. ..................... 600/544; 600/546; 600/301; 128/920; 340/575

(58) Field of Search .................. 600/300–301, 600/544–545, 558, 546, 26, 27; 128/903–905, 920–921, 897; 340/575–576, 573.1, 825.9; 180/271–272; 701/301; 351/200

(56) References Cited

U.S. PATENT DOCUMENTS

| | | |
|---|---|---|
| 4,171,696 A | 10/1979 | John |
| 4,279,258 A | 7/1981 | John |
| 4,928,704 A | 5/1990 | Hardt |
| 4,955,388 A | 9/1990 | Silberstein |
| 5,154,180 A | 10/1992 | Blanchet et al. |
| 5,263,487 A | 11/1993 | Sakamoto et al. |
| 5,311,877 A | 5/1994 | Kishi |
| 5,447,166 A | 9/1995 | Gevins |
| 5,513,649 A | 5/1996 | Gevins et al. |
| 5,601,090 A | 2/1997 | Musha |
| 5,626,145 A | 5/1997 | Clapp et al. |
| 5,649,061 A | 7/1997 | Smyth |
| 5,678,560 A | 10/1997 | Sakamoto et al. |
| 5,729,205 A | 3/1998 | Kwon |
| 5,762,611 A | 6/1998 | Lewis et al. |
| 5,786,765 A | 7/1998 | Kumakura et al. |
| 5,813,993 A | 9/1998 | Kaplan et al. |
| 5,999,846 A | 12/1999 | Pardey et al. |
| 6,001,065 A | 12/1999 | De Vito |
| 6,032,072 A | 2/2000 | Greenwald et al. |

FOREIGN PATENT DOCUMENTS

EP  0 699 413 A1  3/1996

OTHER PUBLICATIONS

Berg, P. et al., *A multiple source approach to the correction of eye artifacts*; Electroencephalography and Clinical Neurophysiology; (1994) vol. 90, pp. 229–241.

(List continued on next page.)

*Primary Examiner*—Max F. Hindenburg
*Assistant Examiner*—Michael Astorino
(74) *Attorney, Agent, or Firm*—Fulwider Patton Lee & Utecht, LLP

(57) ABSTRACT

The method for the quantification of EEG waveforms along the alertness continuum involves collecting and transforming EEG signal data, identifying and rejecting or decontaminating epochs containing various artifacts, and classifying individual EEG patterns along an alertness-drowsiness continuum. The results of the multi-level classification system are applied in real-time to provide feedback to the user via an audio or visual alarm, or are recorded for subsequent off-line analysis.

13 Claims, 16 Drawing Sheets

OTHER PUBLICATIONS

Brunia, C. et al., *Correcting ocular artifacts in the EEG: a comparison of several methods*; Journal of Pyschophysiology ; (1989) vol. 3, pp. 1–50.

Hatskevich, C. et al., *Off–line methods for detection and correction of EEG artefacts of various origin*; Int'l Journal of Psychophysiology; (1992), vol. 12, pp. 179–185.

Sadasivan, P.K. et al., *Minimization of EOG Artefacts From Corrupted EEG Signals Using a Neutral Network Approach*; Comput. Biol. Med., vol. 24, No. 6, pp. 441–449.

Woestenburg, J.C., et al., *The Removal of The Eye–Movement Artifact From The EEG By Regression Analysis in the Frequency Domain*; Biological Psychology, Vol 16 (1983) pp. 127–147.

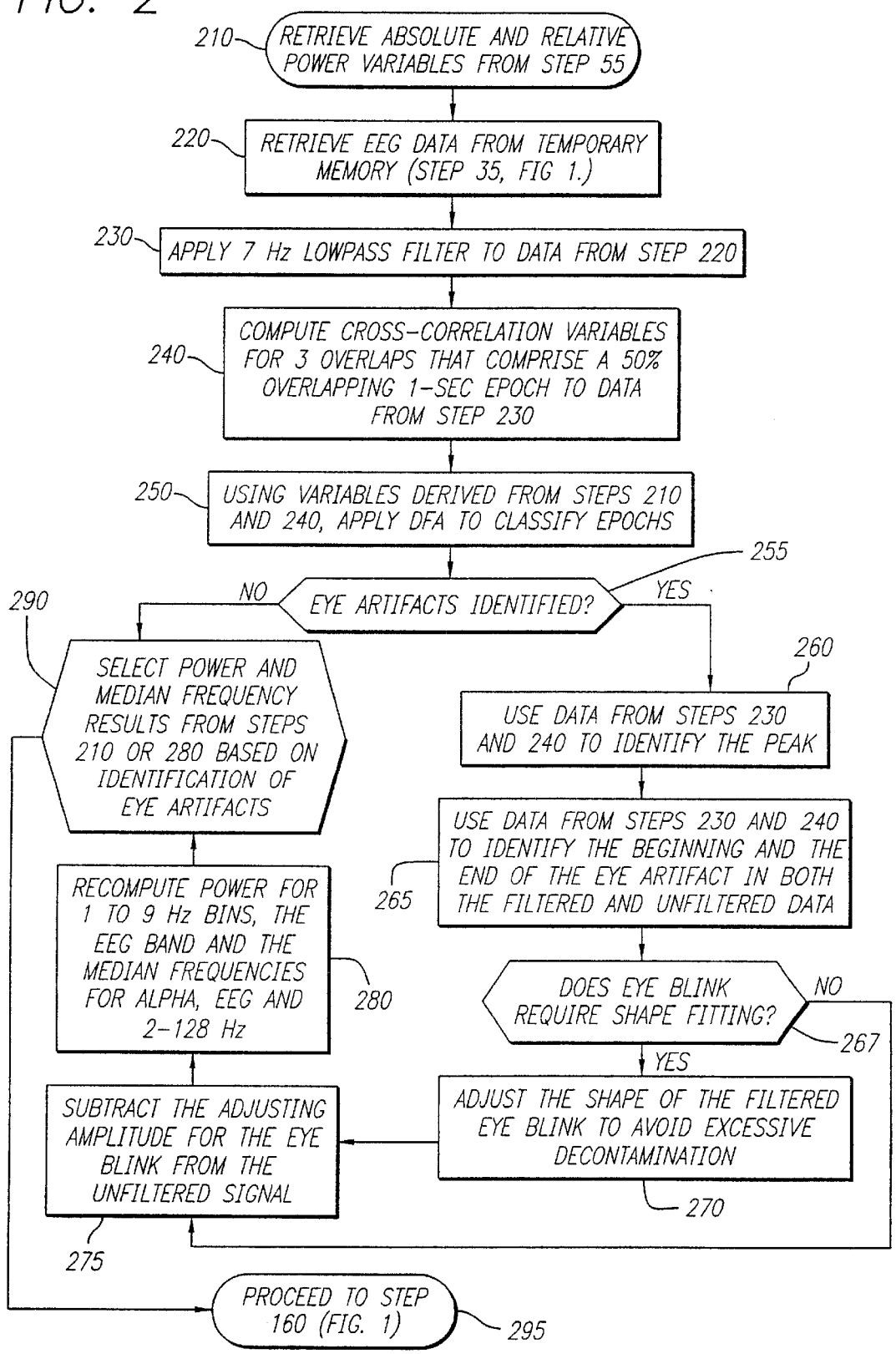

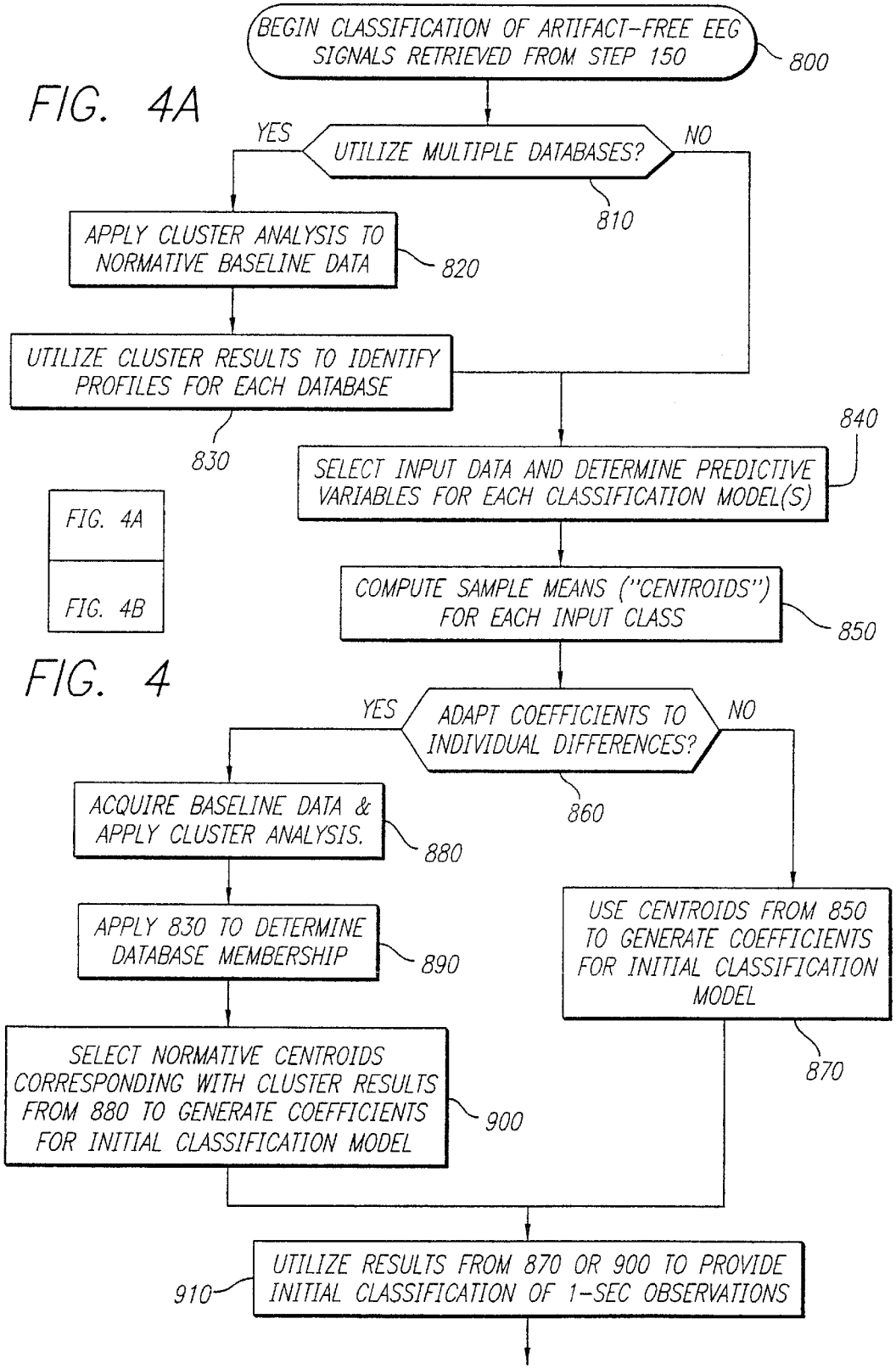

METHOD FOR THE QUANTIFICATION OF HUMAN ALERTNESS

RELATED APPLICATIONS

This application is a divisional of Ser. No. 09/345,046 now U.S. Pat. No. 6,496,824, filed Jun. 30, 1999, which is based upon Provisional Application Ser. No. 60/114,528, filed Dec. 31, 1998.

The United States Government has rights to this invention pursuant to research supported in whole or in part by NIH contracts R43NS6344 and N43NS72367 and grant R43NS35387 awarded by the National Institute of Neurological Disease and Stroke.

BACKGROUND OF THE INVENTION

1. Field of the Invention

This invention relates generally to analysis of electroencephalograms, and more particularly concerns a method for quantifying and monitoring human alertness.

2. Description of Related Art

An electroencephalogram (EEG) measures electrical activity of the brain. Since the electrical activity of the brain first started to be recorded, efforts have been made to identify how the EEG data correlates with behavior, mood, mental performance, attention, and vigilance. However, classifying changes in the state of alertness, drowsiness, mental performance, or attention has proven difficult due to the significant variability of the EEG for an individual and between individuals, even under controlled conditions.

The frequencies of the waking EEG have generally been organized into three bands (or bandwidths): the theta band (4 to 7 Hertz ("Hz")), the alpha band (8 to 13 Hz) and the beta band (14 to 24 Hz). When a person is fully rested and undertakes a cognitive task, the EEG amplitude is relatively small overall, power in the alpha band is suppressed, and the power in the frequencies above 13 Hz (i.e., beta band) tend to increase. As a person becomes tired, the overall amplitude of the EEG and the power in the frequencies below 13 Hz increase (i.e, alpha and theta bands). As sleep onset approaches, first dominant alpha activity followed by distinct theta become apparent. Momentary fluctuations between states are observed in the EEG when a person is tired or sleep deprived and is trying to remain awake.

The real-time quantification of an individual's state of alertness has a number of commercial applications. Shift workers, truck drivers, train operators and other individuals who work during normal hours of maximum sleepiness could be notified when they become too drowsy. In addition, these workers could be notified when a short-nap would be most beneficial in managing their fatigue. Pilots, air traffic controllers and other workers who perform monotonous tasks could be notified when they begin to daydream or are not maintaining an acceptable level of alertness. The EEG of adults and children with Attention Deficit Disorders or Attention Deficit/Hyperactivity Disorders could be monitored to assist them in maintaining a normal state of alertness. The recording and subsequent off-line analysis of the EEG to assess alertness over wider time intervals can be used to assess treatment outcomes for patients with sleep disorders, to titrate dosages of prescription drugs, and to measure the effects of new pharmacological substances on alertness.

The quantification of states of alertness, drowsiness, mental performance, and so on, are complicated by significant differences in the EEG observed between individuals during similar tasks, in addition to changes within individuals as a result of circadian rhythms and other fluctuations. One approach to overcome the issue of variability between individuals in the amplitude and distribution of the EEG power has been to develop paradigms whereby the individual can be used as his or her own control. For example, Gevins et al. (U.S. Pat. No. 5,447,166) monitors neurocognitive workload based on the individual's normative neurocognitive calibration function acquired during a specific battery of tasks. The present inventors have realized that this normalization technique is limited, however, when conditions are not highly controllable. For the monitoring of alertness across the multitude of activities and conditions common to daily living, for example, users would need to be measured during multiple sessions to acquire baseline values representing the continuum from highly alert to sleep onset.

An alternative approach has been to develop a classification model using EEG variables which have been transformed to minimize individual differences. The most common transformation technique standardizes the EEG variables for each observation or time period of data analyzed (i.e., epoch) relative to the mean and standard deviations for the particular session or a baseline session (i.e., Z-scores). This normalization technique is limited, however, when monitoring the continuum from fully alert to sleep onset, because there is no single session or activity that best categorizes the diversity in patterns of distribution of power across the EEG frequency bins, individuals, and tasks. Standardizing the EEG based on the amplitude and distribution of power during sessions where the individual is awake with eyes closed, for example, reduces variability in the alpha range across subjects. However, the present inventors have recognized that this approach does not normalize population differences with respect to increased beta power during cognitive tasks. Misidentification of the state of alertness will inevitably occur along the alertness-drowsiness continuum unless techniques are developed to first identify individual patterns in the distribution of the EEG, and then adapt the model to overcome these differences. The methods of the present invention solve these problems.

Another problem complicating the monitoring of the EEG and classifying the state of alertness along the alertness-drowsiness continuum is the contamination of the EEG recording by artifacts resulting from eye blinks and ocular movements. These artifacts are problematic because the power resulting from eye artifacts cannot be readily differentiated from power contributed by theta activity in the frequency domain. As mentioned previously, the onset of sleep is categorized by increased or dominant activity in the theta range of power between 4–7 Hz. Fast blinks that rewet the eyes typically range from 0.20 to 0.30 seconds in duration and cause contamination by increasing the power in the 3 to 5 Hz bins. Slower eye blinks or closures that occur when a subject becomes tired, range from 0.30 to 1 second in duration and cause contamination by increasing the power in the 1 to 4 Hz bins. Frequency bins above 5 Hz can also be affected, depending on the amplitude and duration of the blink.

Epochs with eye artifact in the EEG can be identified and automatically rejected from the analysis by monitoring significant variations in EEG amplitude. This approach, however, as the present inventors have recognized, results in an excessive amount of data being rejected when eye movements are detected. Alternatively, the power below 5 Hz can be high-pass filtered to eliminate both the eye artifact and the theta activity. The present inventors have recognized that this approach results in the exclusion of variables that are highly correlated with alertness. A number of methods have been developed to remove the eye artifact from the EEG in the time-domain based on comparison with signals acquired simultaneously from electro-oculographic (EOG) recording or eye motion sensors. For applications that acquire EEG during activities of daily living, however, placement of EOG electrodes near the eye(s) would be uncomfortable and cosmetically unacceptable. The use of an eye motion sensor would only be appropriate when the user's movement is limited, such as when seated in the cockpit of an airplane or vehicle. In the acquisition of EEGs during activities of daily living, additional artifacts are typically encountered which can result in a failure to correctly identify the individual's state of alertness. Electromyographic (EMG) activity, spikes and amplifier saturation can cause a substantial increase in power that distorts the entire EEG band. Gross head, eye or body movements result in artifacts that increase the power in the slower frequencies (i.e, less than 4 Hz). Procedures should be developed which automatically detect, as well as monitor, the occurrence of these artifacts in order to maximize the amount and quality of data acquired real-time or off-line analysis.

Another problem encountered when analyzing the EEG in the frequency domain is the non-stationary effects (i.e., momentary fluctuations) of the EEG itself. One approach to reduce the variability of the EEG power on a second by second basis is to average several seconds of data. However, if the EEG data are averaged across too many seconds, fluctuations that are predictive of a changing state of alertness may no longer be apparent. Accordingly, a method is needed to improve the resolution of the averaged EEG data across a shorter period of time. The present invention meets these and other needs.

SUMMARY OF THE INVENTION

Briefly, and in general terms, the present invention provides for a method for the quantification of EEG waveforms along the alertness-drowsiness continuum. A preferred method comprises the steps of:

1) Collecting and transforming data—EEG signals are acquired at 256 samples per second from a plurality of electrode sites, but preferably from Cz, Pz and Oz according to the International 10–20 system. A linear transform is applied to eliminate contribution in the power from DC offset. A Kaiser $\alpha=6.0$ windows for power calculations provides superior spectral resolution compared to commonly used windows for EEG data processing, including Blackman, Cosine Taper, Boxcar or Harming. The data are zero-padded and a 1,024 point fast Fourier transform (FFT) is applied to each one second epoch to generate power results at 0.25 Hz intervals. A 50% overlapping window is utilized to smooth the between-epoch power attributed to non-stationarity of the EEG. The power is then computed for 1 Hz bins between 1 and 24 Hz., as well as median frequencies for the conventional EEG bands (i.e., theta, alpha, beta) to optimally identify changes in the EEG that correlate with alertness and drowsiness.

2) Identifying and rejecting or decontaminating epochs containing various artifacts such as amplifier saturation, spikes or excursions, electromyographic (EMG) activity, and/or gross head, eye or body movement.

3) Identifying and eliminating eye artifacts. Eye blinks, or eye artifacts are identified using discriminant function analysis and eliminated using only the EEG signal as the input, in real-time or off-line, without the aid of additional eye monitors or the like.

4) Classifying individual EEG patterns along the alertness-drowsiness continuum, preferably using discriminant function analysis to implement a multi-level classification model. The first level classifies the state of alertness for each one second epoch as High Vigilance, Low Vigilance, Eyes Closed, or Sleepy. The second level provides sub-categorization or further refinement of the first level classifications. The third level applies a multi-dimensional time-series analysis, using the results from the initial classification and sub-categorization analyses from multiple epochs, to further define states of alertness that correlate with performance.

5) Applying the results of the multi-level classification system in real-time to provide feedback to the user via an audio or visual alarm. Alternatively, EEG data could be recorded and the multi-level classification system applied off-line to provide information pertaining to the number and duration of drowsy episodes. These results could be used to assess treatment outcomes from sleep disorder patients, monitor children and adults with attention deficit or hyperactivity disorders, and/or assess the effects of pharmacological drugs. Other applications are also possible.

Accordingly, one or more of the following are objects of a method of the present invention:

to provide a method for the analysis of the EEG which identifies and rejects or decontaminates epochs containing artifacts such as EMG activity, movement activity, amplifier saturation, spikes or excursions, in real-time or off-line;

to provide a method for the analysis of the EEG which monitors epochs containing artifacts such as EMG activity, movement activity, amplifier saturation, spikes or excursions in real-time and notify the user when certain thresholds are being crossed;

to provide a method for the analysis of the EEG which identifies and decontaminates eye blink artifacts from the EEG data using only the EEG signal as the input, in real-time or off-line;

to provide a method for the analysis of EEGs which implements discriminant function analysis to obtain a multi-level classification model along the alertness-drowsiness continuum, in real-time or off-line;

to provide a method for the application of classified EEG data to real-time monitoring of alertness and notifying the user when certain thresholds are being crossed;

to provide a method for recording EEG data for subsequent analysis.

These and other aspects and advantages of the invention will become apparent from the following detailed description and the accompanying drawings, which illustrate by way of example the features of the invention.

BRIEF DESCRIPTION OF THE DRAWINGS

FIG. 1, including sub-components

FIG. 2 is a block diagram illustrating an eye blink identification and decontamination method.

FIG. 4, including sub-components FIGS. 4A and 4B, is a block diagram illustrating a method for classifying alertness using a multi-level model.

DETAILED DESCRIPTION OF THE PREFERRED EMBODIMENTS

Turning in detail to the drawings, FIG. 1 illustrates a top level flow chart for the preferred embodiment of the present invention.

I. Data Acquisition and Transformation

A. Data Acquisition

Figure 6:
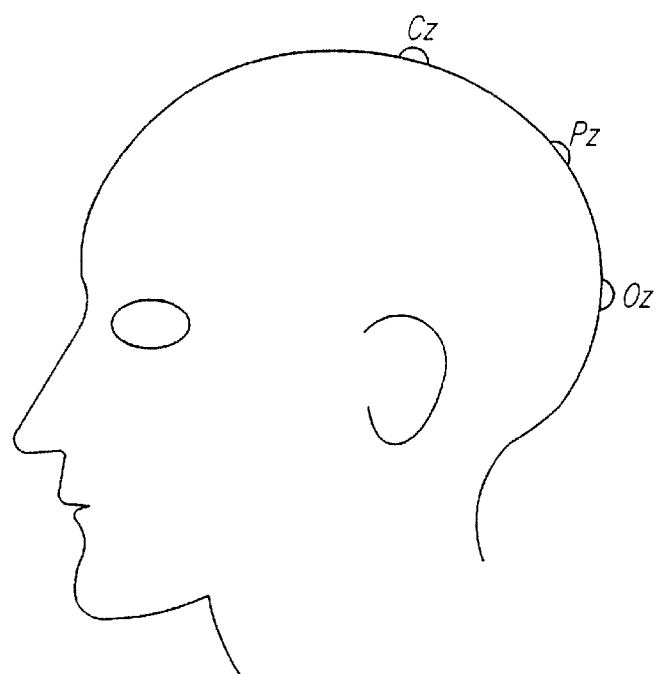
FIG. 6 is a schematic illustrating the electrode locations according to the preferred method of the present invention.

To begin the analysis process, electroencephalographic (EEG) data are first acquired 10). A plurality of electrodes are placed at various locations on the subject's head. In the preferred embodiment, the electrode sites are at Cz, Pz and Oz according to the International 10–20 System as shown in FIG. 6. To obtain high quality signals using conventional EEG electrodes, the hair must be parted and the scalp prepared prior to seating the electrode. An abrasion cream (e.g., Nu-Prep, D.O. Weaver & Co., Aurora, Colo.) and Q-tip can be used to prepare the scalp by removing the top layer of dead skin. The electrodes must be securely affixed to the scalp with a conductive material making contact between the electrode and the scalp in order to achieve and maintain electrode impedance values preferably below 5 k$\Omega$. Alternatively, pre-amplifiers or active electrodes with very high input impedance (i.e., greater than $10^{10}$ ohms) can be used to minimize the need for scalp preparation. In either case, the electrodes would need to be affixed to the scalp in order to minimize artifact.

The preferred system for making ambulatory recordings is a portable, battery powered digital recorder. The amplifiers should be low powered and a gain selected that provides the best signal resolution while minimizing the occurrences of amplifier saturation. The low-powered amplifiers described in U.S. Pat. No. 5,678,559, herein incorporated by reference, may provide these characteristics. An analog to digital converter (A/D chip) and the capability to store the data in a digital format is required (e.g., flash memory). To monitor artifact or classify alertness in real-time, a digital signal processing chip (DSP chip) is necessary. The apparatus described in U.S. Pat. No. 5,645,068, herein incorporated by reference, may provide these capabilities.

The inventors have determined that bi-polar recordings generate significantly less artifact under ambulatory conditions, as compared to mono-polar recordings. The inventors determined that one second observations (i.e, epochs) should be sampled at 256 samples per second.

For some ambulatory recording sessions, electrooculograms (EOG) may also be acquired to identify eye movement. EOG electrodes are applied in a manner similar to the methods described above for the vertical (i.e, above the eye) and horizontal (i.e, outside the eye) placements. The amplifier gain and sampling rate for EOG recordings can be set lower for EEG recordings.

In the preferred embodiment, the analysis described below is performed in real time. However, the data can also be acquired and stored for future, off-line analysis (step 15). If this path is chosen, the offline analysis can nevertheless follow the steps outlined in FIG. 1

B. Identification and Elimination of Artifacts

To begin the data analysis, a determination can be first made of whether the data is contaminated with amplifier saturation (step 20). Sudden head or body movements can result in artifact of sufficient magnitude that results in amplifier saturation. Degradation of electrode quality can also result in amplifier saturation. Saturation artifact generally results in a level of contamination across the EEG frequencies that causes misclassifications. Thus, epochs with saturation should be rejected. The effects of saturation can also extend to the beginning data points of the subsequent epoch. In these cases, an overall downward (upward) trend in the amplitude of the data points occurs, resulting in an increase in power in the slower frequencies (i.e., 0–6 Hz) until the EEG signal returns to a stable state.

In the preferred embodiment, the data is analyzed to identify and eliminate epochs containing amplifier saturation. However, this analysis is not absolutely necessary. If the analysis is not conducted, then the data, which is still in the time domain, can be analyzed for spikes or excursions (step 32). If the analysis is conducted to identify and eliminate data with amplifier saturation (step 30), however, the process of FIG. 3A is followed.

Figure 3A:
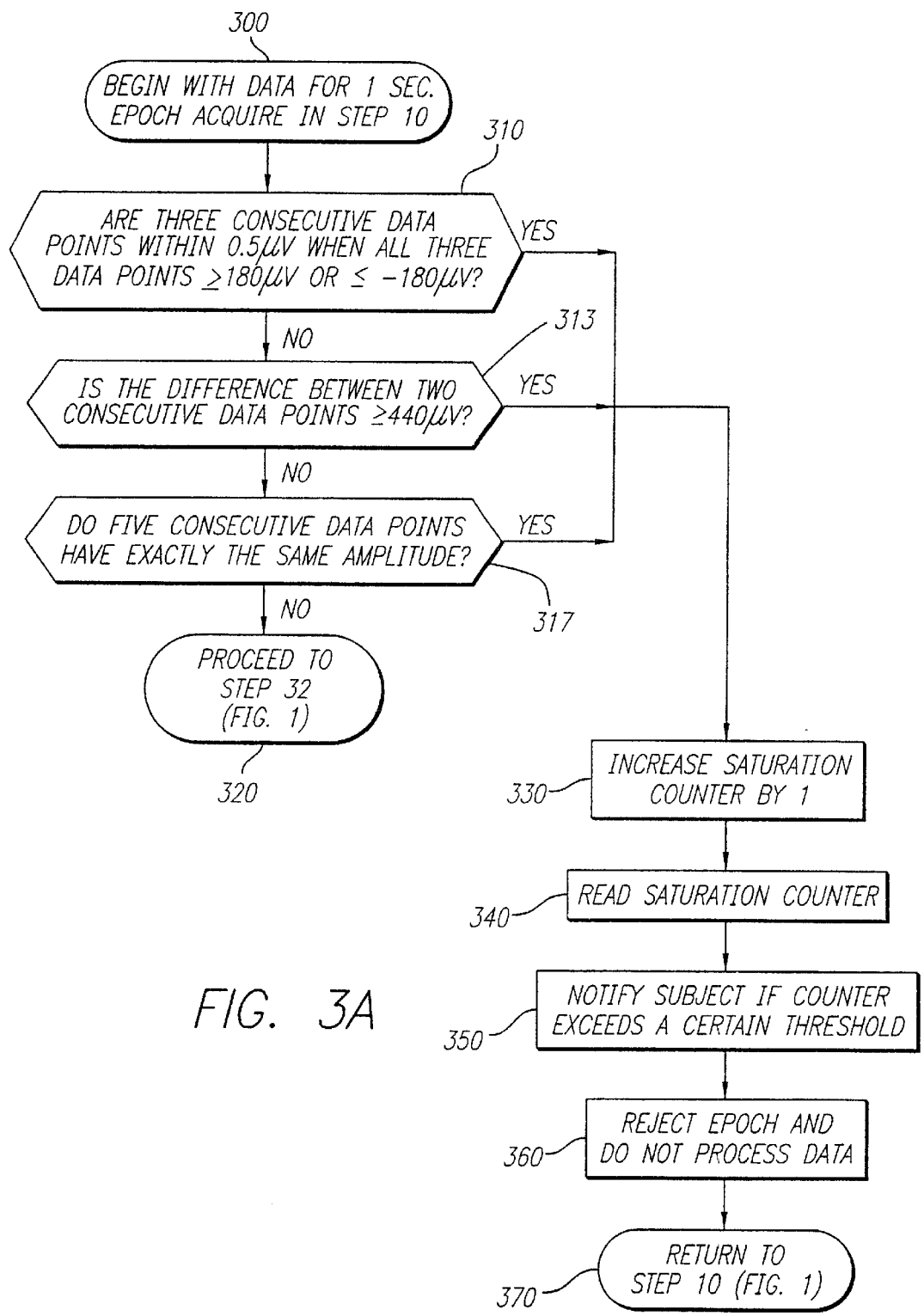
FIG. 3A is a block diagram illustrating an amplifier saturation identification and elimination method.
Figure 8A:
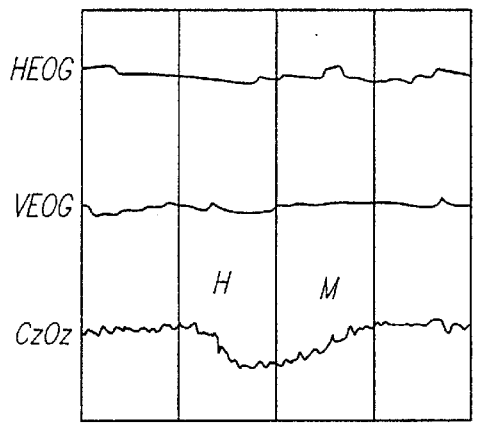
FIG. 8A is a graph depicting EEG data (four, one second epochs) with low ("L"), medium ("M"), or high ("H") levels of movement artifact.
Figure 8B:
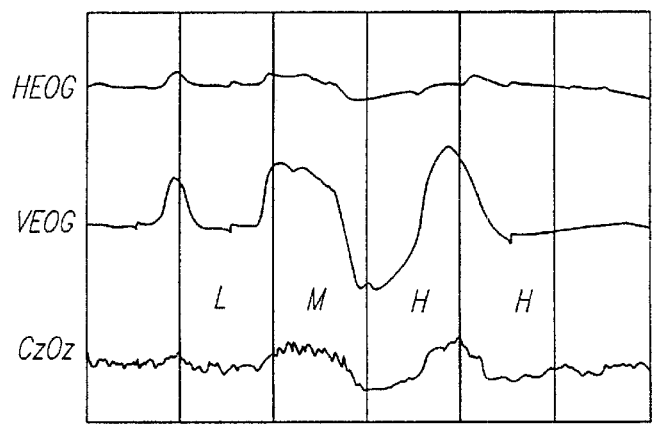
FIG. 8B is a graph depicting EEG data (six, one second epochs) with low ("L"), medium ("M"), or high ("H") gross eye blink artifact.
Figure 8C:
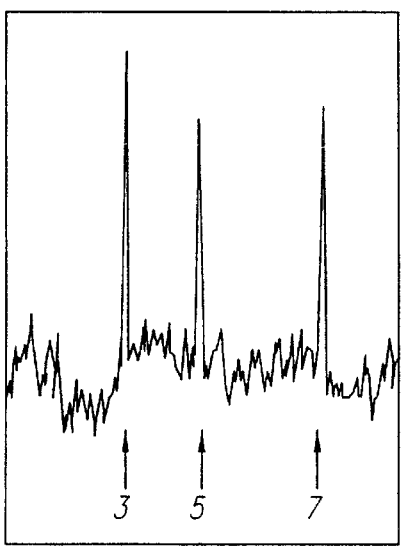
FIG. 8C is a graph depicting EEG data with 3, 5, and 7 data point spikes.

Turning in detail to FIG. 3A, first determine whether any of the following rules are violated: (a) Three consecutive data points are within 0.5 µV and all three data points are greater than or equal to 180 µV or less than or equal to −180 µV (step 310) (See also FIG. 8E); (b) five consecutive data points have exactly the same amplitude (µV value) (step 317) (See also FIG. 8F); or (c) The difference between two consecutive data points is greater than or equal to 440 µV (step 313) (See also FIG. 8G).

If none of these rules are violated, then the data is acceptable and the process can continue with an analysis of the epoch to identify spikes and excursions (step 320). If one of these rules is violated, on the other hand, than the data is contaminated with amplifier saturation. Accordingly, the saturation counter should be increased by one (step 330). Then the counter is read (step 340) and, if a certain threshold set to minimize the number of epochs rejected for saturation is exceeded, the subject is notified by an audio and/or visual alarm (step 350). The epoch containing amplifier saturation is rejected and the epoch is not processed any further (step 360).

Figure 1A:
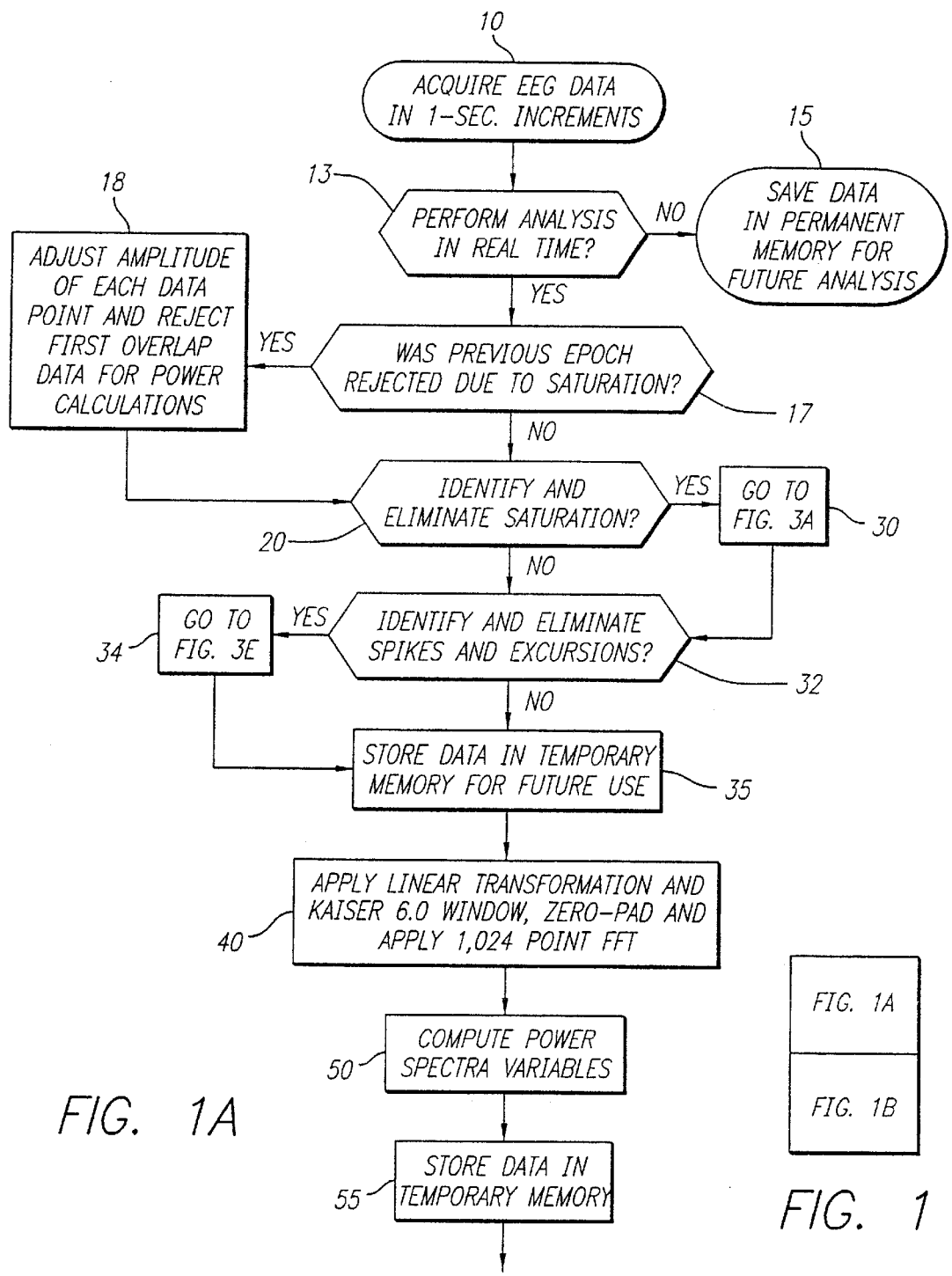
FIGS. 1A and 1B, is a block diagram illustrating the method of the present invention.
Figure 1B:
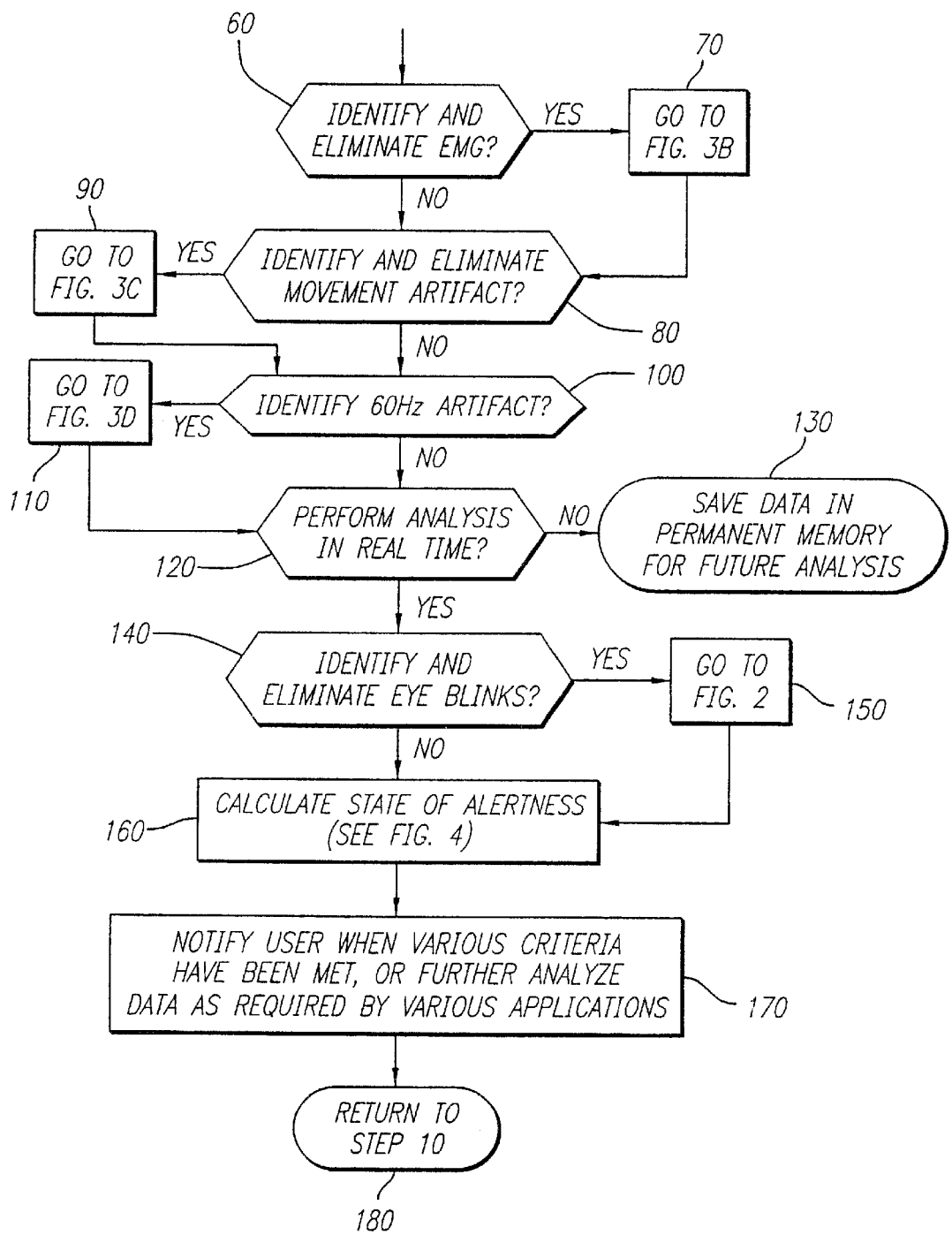

The analysis then starts anew with the next epoch from step 10 of FIG. 1 (step 370). However, the effects from saturation in the previous epoch can result in artifact in the subsequent epoch(s) until the EEG signal returns to a stable state. To decontaminate this artifact, implement the following steps for the epoch subsequent to an epoch rejected for saturation (steps 17 and 18 in FIG. 1A): (a) compute the mean amplitude for the first five ("mean b-point") and the last five ("mean e-point") data points in the second overlap of the epoch; (b) compute the slope between the mean b-point and mean e-point [(mean b-point−mean e-point)/number of data points of overlap (256)]; (c) if the slope computed in step c$\geq$0.2 for the second overlap (i.e, ~50 µV), then adjust the amplitude of each data point in the second overlap, to that end, compute the "adjusting amplitude" of each data point affected by the saturation based on the difference between the computed slope and a slope of zero, and adjust the amplitude of each data point in the second overlap by subtracting the adjusting amplitude; and finally (d) compute the power for the one second epoch using the adjusted second and third overlaps. It is noted that the first overlap from the previous epoch that was rejected for saturation should not be used. For these epochs, the analysis continues with an identification and elimination of amplifier saturation as described above (step 20).

Epochs that have not been discarded as contaminated with amplifier saturation are then processed further to determine whether they contain spike or excursion artifacts. Spike artifacts are commonly caused by brief disruptions in the scalp-electrode interface, such as when the electrode shifts or slides when the user is walking. Spikes or excursion artifacts can also result when the electrode is tapped, bumped or touched. Excursions can also be caused by abrupt head or body movements. If desired, the data can be analyzed to identify and decontaminate spikes and excursions (step 32). Sudden changes in amplitude greater than 60 µV result in spike or excursion artifacts that are generally not associated with normal EEG activity. In the preferred embodiment, the data are analyzed to identify and decontaminate epochs with spikes and excursions. However, alternative embodiments need not do so. If the analysis is not performed, the epochs not eliminated due to amplifier saturation can be stored in temporary memory for future use (step 35).

The increase in power that results from spike or excursion artifacts is influenced by the amplitude and/or the number of data points which contribute to the artifact. A one-data point spike tends to affect the power in frequencies greater than 20 Hz. Spike artifacts that develop over five or more data points or excursions tend to contaminate the power across all frequencies in the EEG band (i.e., 1–24 Hz).

It is not uncommon for EMG artifacts also to contribute to sudden changes in amplitude greater than 60 µV. However, spike artifacts tend to be isolated to a few occurrences in a one second epoch. While spikes tend to be isolated to a relatively small number of data points (i.e., fewer than 8), excursions can affect the amplitude of numerous data points subsequent to the excursion. Both spike and excursion artifacts can be decontaminated, however, so that the epoch can be utilized for further analysis.

Figure 3B:
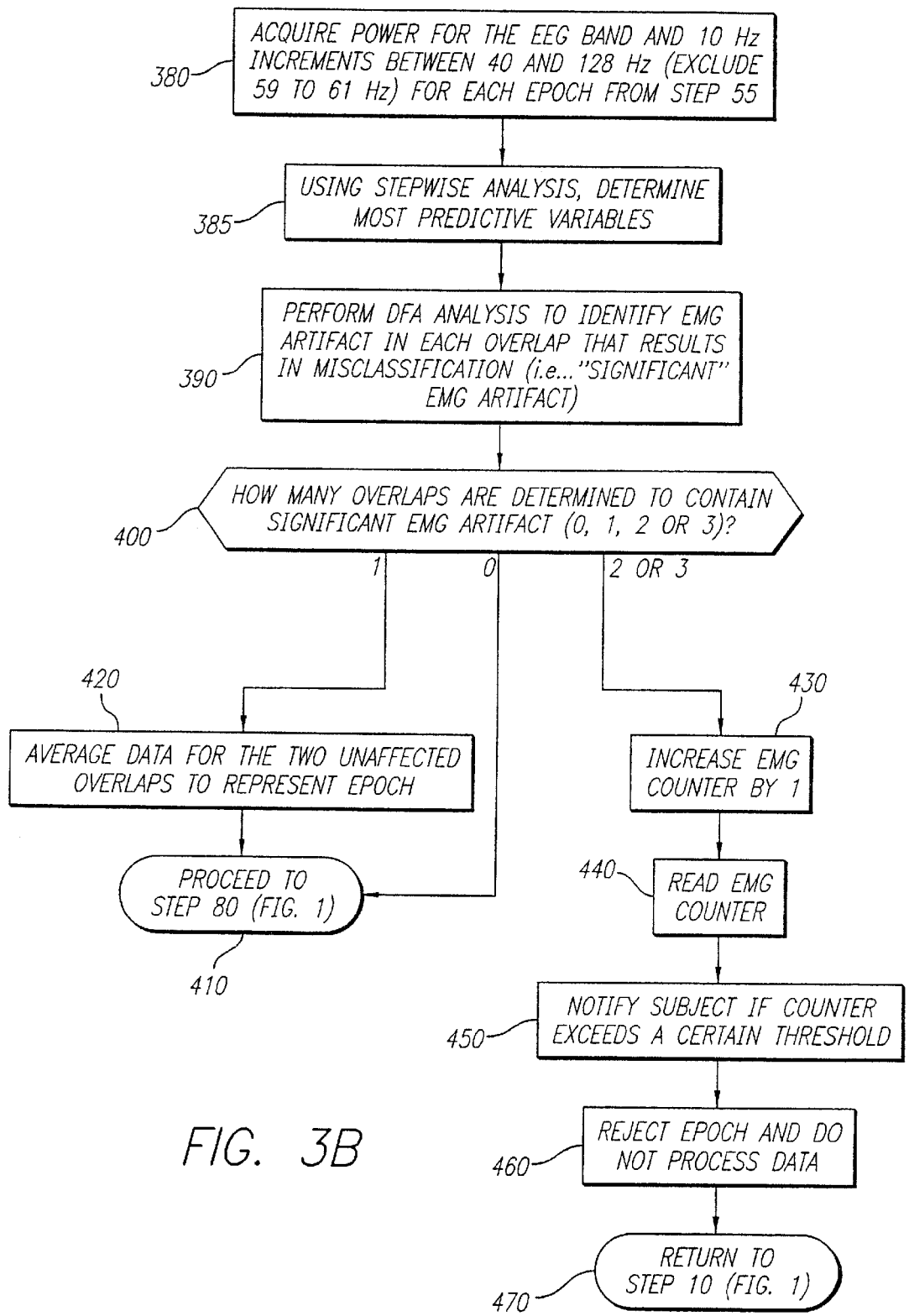
FIG. 3B is a block diagram illustrating an EMG identification and elimination method.
Figure 3C:
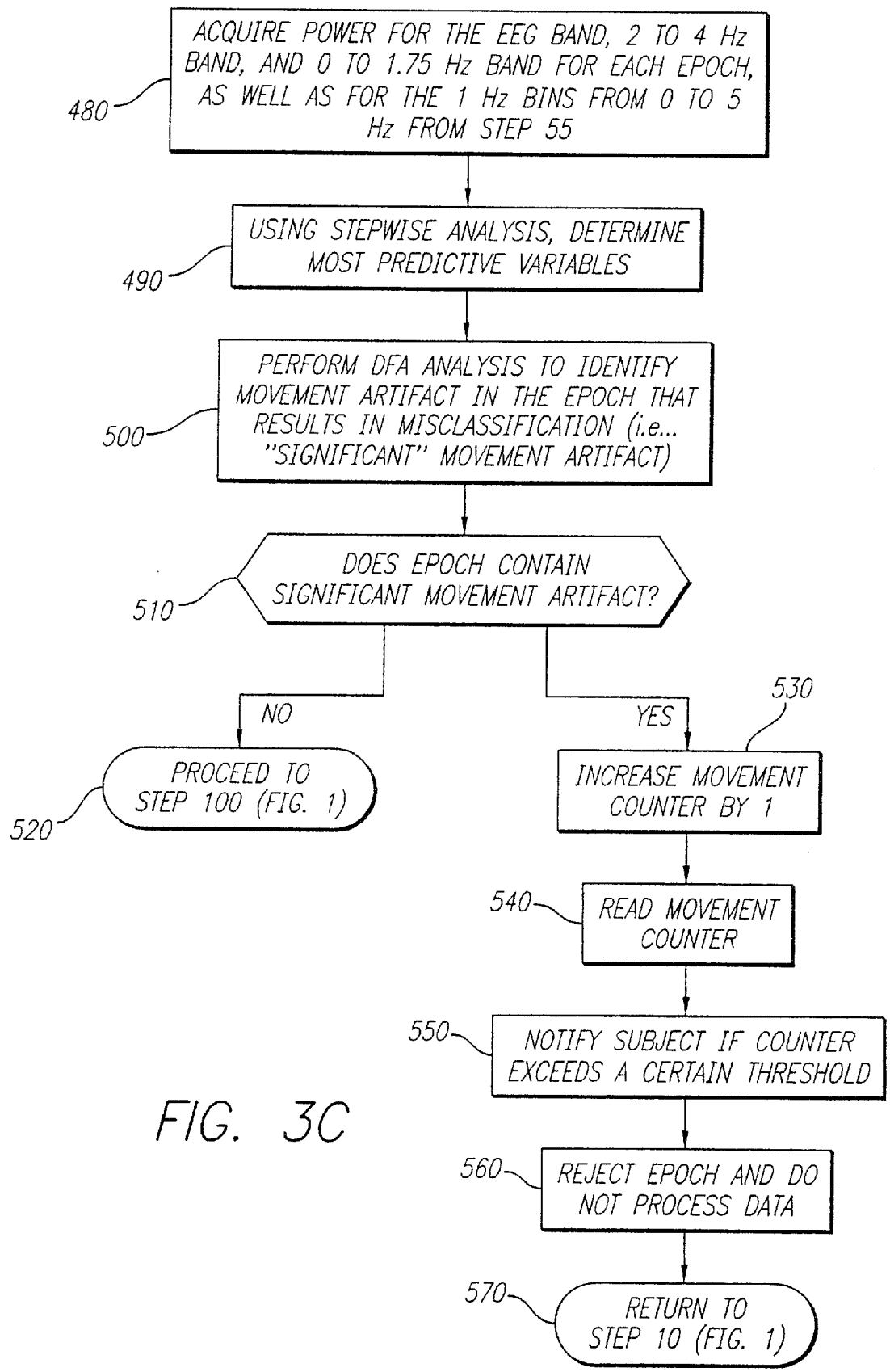
FIG. 3C is a block diagram illustrating a movement artifact identification and elimination method.
Figure 3D:
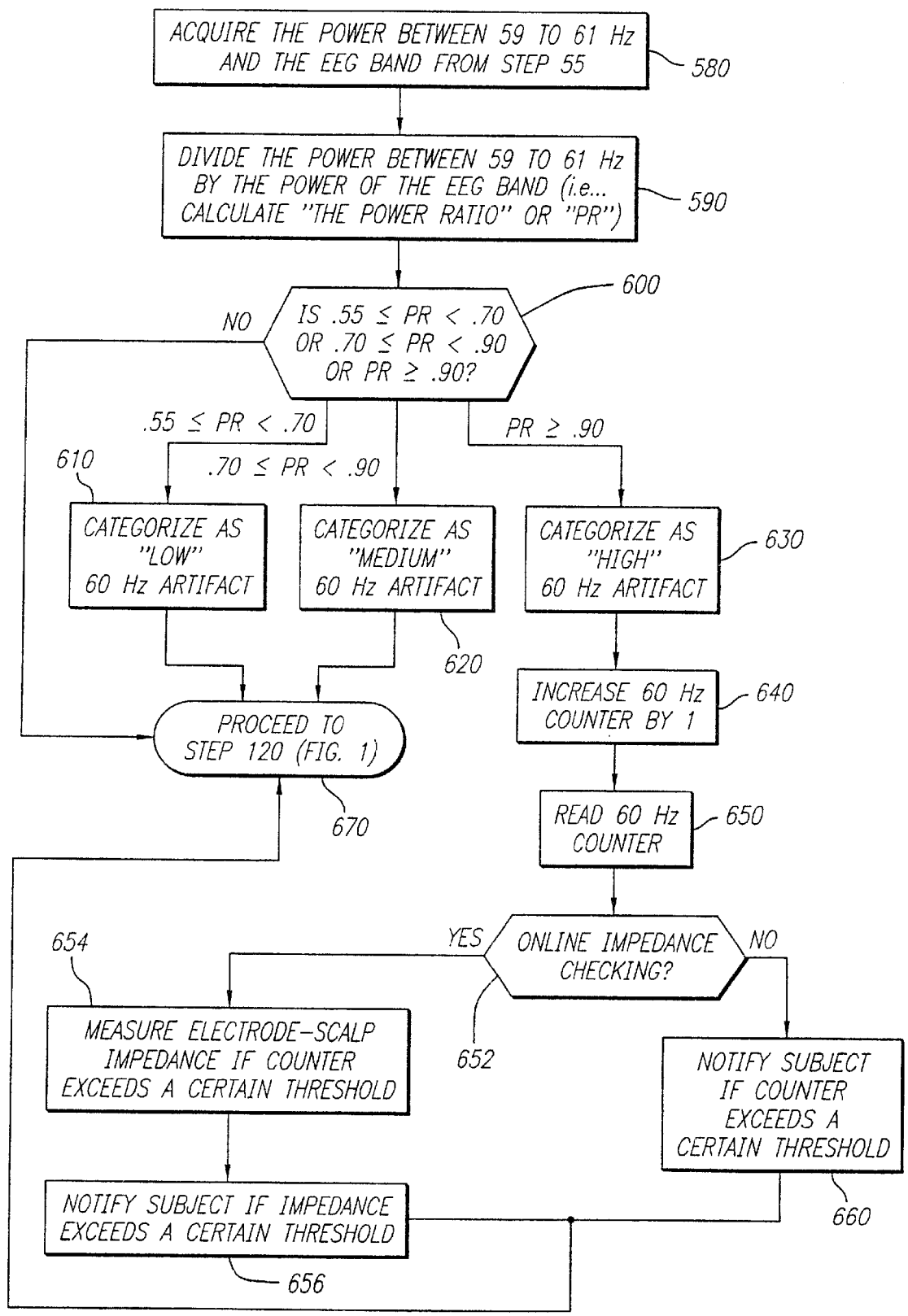
FIG. 3D is a block diagram illustrating a 60 Hz artifact identification method.
Figure 3E:
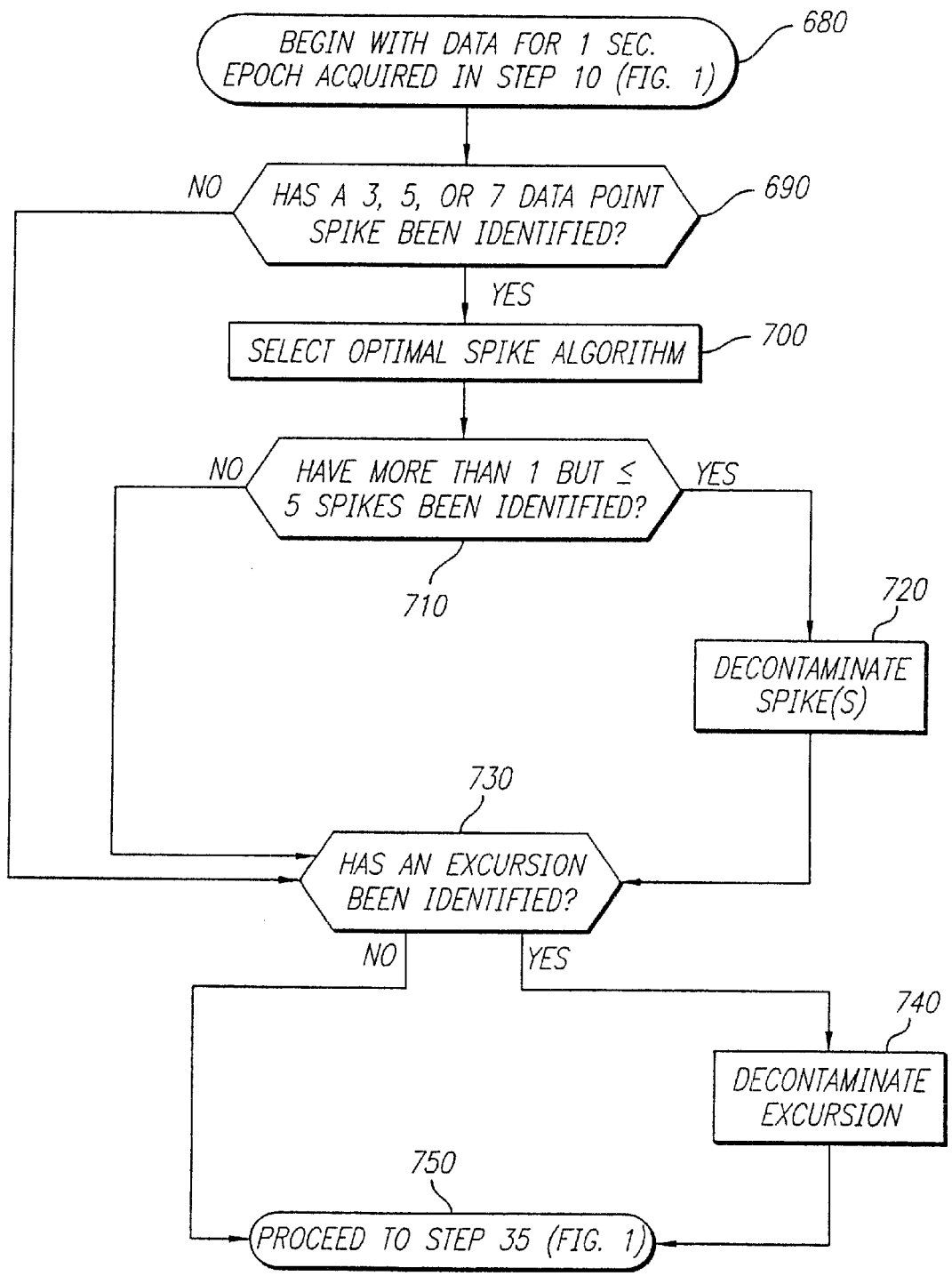
FIG. 3E is a block diagram illustrating a spike and excursion artifact identification and decontamination method.

If spikes and excursion artifacts are to be identified and decontaminated, the steps outlined in FIG. 3E can be followed (step 34). Turning in detail to FIG. 3E, therefore, the data is first analyzed to determine whether the epoch contains a 3, 5, or 7 data point spike (step 690) (See FIG. 8C for an illustration of the three types of spikes). A 3-data point spike exists if: (a) the absolute value of the amplitude of [data point$x$ subtracted from $x-1$]$\geq$60 µV, and (b) the absolute value of the amplitude of [data point$x$ subtracted from $x+1$]$\geq$60 µV. A 5-data point spike exists if: (a) the absolute value of the amplitude of [data point x subtracted from $x-2$]$\geq$60 µV, and (b) the absolute value of the amplitude of [data point$x$ subtracted from $x+2$]$\geq$60 µV, and (c) $x>x-1$ and $x-1>x-2$ and $x>x+1$ and $x+1>x+2$, or $x<x-1$ and $x-1<x-2$ and $x<x+1$ and $x+1<x+2$. Finally, a 7-data point spike exists if: (a) the absolute value of the amplitude of [data point$x$ subtracted from $x-3$]$\geq$60 µV, and (b) the absolute value of the amplitude of [data point$x$ subtracted from $x+3$]$\geq$60 µV, and (c) $x>x-1$ and $x-1>x-2$ and $x-2>x-3$ and $x>x+1$ and $x+1\geq x+2$ and $x+2>x+3$, or $x<x-1$ and $x-1<x-2$ and $x-2<x-3$ and $x<x+1$ and $x+1<x+2$ and $x+2<x+3$.

Next, the optimal spike algorithm is selected (step 700). In some cases, a spike may be identified by more than one spike rule (i.e., both 5- and 7-data point spike rules may be violated). The optimal spike decontamination rule is determined by: (a) determining the absolute value of the difference between the amplitude of the data points corresponding with the beginning and the end of the spike for each rule that is violated (e.g., [(x−1)−(x+1)], [(x−2)−(x+2)], [(x−3)−(x+3)]); and, (b) selecting the algorithm with the smallest absolute value calculated in the previous step.

If the data contains no spikes, or contains more than five spikes, it need not be decontaminated (step 710). The analysis can continue with the identification and decontamination of excursions (step 730). It is noted that if more than five spike artifacts are identified in one 256 data point overlap, then the spikes do not need to be decontaminated. After application of the EMG artifact rules (see below), the epoch should be rejected. Otherwise, the data can be decontaminated of spikes (step 720) by the steps of: (a) determining the amplitude of the data points corresponding with the beginning (x−1, x−2 or x−3) and the end (x+1, x+2 or x+3) of the spike; (b) determining the slope between the data points corresponding with the beginning and end of the spike; (c) determining the "adjusting amplitude" for each data point of the spike based on the difference between the amplitude of each data point of the spike and the corresponding amplitude of the slope line (between the beginning and end of the spike); and (d) adjusting the amplitude of each data point of the spike by subtracting the adjusting amplitude.

Figure 8D:
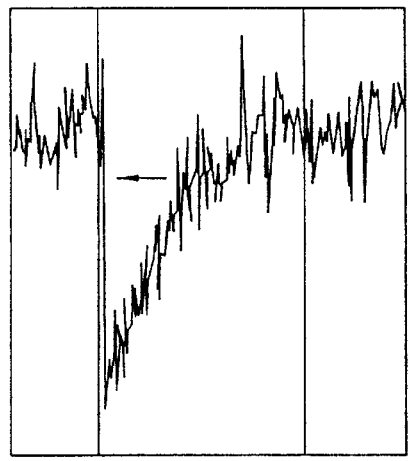
FIG. 8D is a graph depicting EEG data with excursion artifact.
Figure 8E:
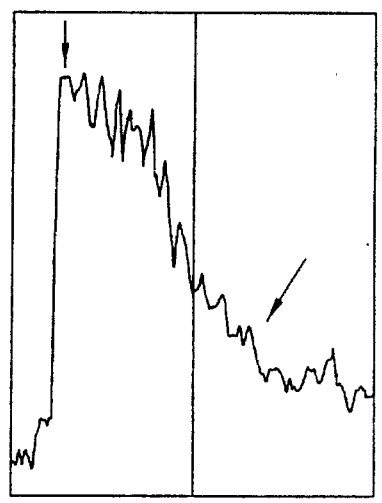
FIG. 8E is a graph depicting EEG data with amplifier saturation identified based on three consecutive data points within a 0.5 $\mu$V range and all >180 $\mu$V (vertical arrow). The second arrow points to the transition from saturation that affects the next epoch.
Figure 8F:
FIG. 8F is a graph depicting EEG data with amplifier saturation identified based on five consecutive data points with the same amplitude (vertical arrow). The second arrow points to the transition from saturation that affects the next epoch.
Figure 8G:
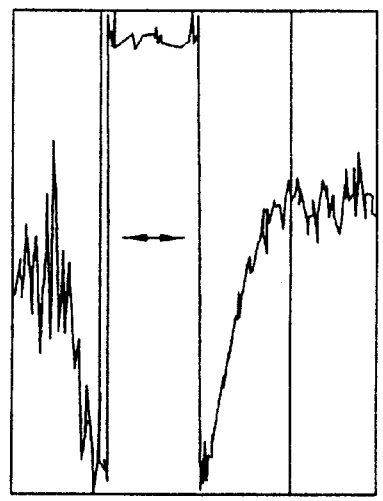
FIG. 8G is a graph depicting EEG data with amplifier saturation identified based on the difference between two consecutive data points >440 $\mu$V (horizontal arrow).

Next, excursions can be identified (step 730). An excursion exists if the absolute value of the amplitude of [data point×subtracted from x−1]≧75 μV and the absolute value of the amplitude of [data point×subtracted from x+1]≧20 μV. FIG. 8D illustrates an excursion artifact. If no excursion exists, the analysis can proceed by storing the data in temporary memory (step 35 of FIG. 1) for later use (step 750). If the data does contain an excursion, the data can be decontaminated (step 740). However, the decontamination approaches are different for real time or off-line analysis. The number of seconds required for the signal to return to a stable state after an excursion is influenced by the amplifiers can take up to three seconds for recovery. With off-line analysis, a number of epochs subsequent to the excursion can be analyzed to determine the exact point when the signal recovers. For the real time analysis, the data should be continuously analyzed, and therefore, feedback as to the user's state of alertness should not be postponed until the signal recovers from an excursion. Decontamination of excursions in real time may, therefore, be less complete compared to off-line analysis, depending on the number of epochs affected by the excursion.

Decontamination of excursions (step 740) for off-line analysis may be accomplished by: (a) determining the mean amplitude for the five data points preceding the excursion (i.e, x−1 through x−5) ("p-mean E"); (b) identifying the first data point ("p-sub E") subsequent to the data point with the excursion with an amplitude ±2 μV of p-mean E; (c) determining the slope between the data points p-mean E and p-sub E which corresponds with all of the data points affected by the excursion; (d) calculating the "adjusting amplitude" based on the difference between the amplitude of each data point affected by the excursion and the corresponding amplitude of the slope line (between the data points p-mean E and p-sub E, as determined the adjusting amplitude. Optionally, the decontaminated data may then be stored in temporary memory for later use (step 750).

Decontamination of excursions (step 740) for real time analysis may be accomplished by: (a) rejecting the epoch that contains the excursion; (b) determining the mean amplitude for the first five data points in the second overlap of the first epoch subsequent to the excursion ("p-mean E"); (c) determining if any data point beginning in the second overlap of the first epoch subsequent to the epoch with the excursion, and ending in the third overlap of the second epoch subsequent to the epoch with the excursion has an amplitude ±2 μV of the p-mean E ("p-sub E"); (d) if rule (c) above is not met, then compute the last five data points of the third overlap in the second epoch subsequent to the excursion ("p-sub E"), (e) determining the slope between the data points p-mean E and p-sub E which corresponds with all of the data points affected by the excursion in the two epochs; (f) calculating the "adjusting amplitude" based on the difference between the amplitude of each data point affected by the excursion and the corresponding amplitude of the slope line (between the data points p-mean E and p-sub E, as determined above); (g) adjusting the amplitude of each data point affected by the excursion by subtracting the adjusting amplitude. Optionally, the decontaminated data may then be stored in temporary memory (FIG. 1, step 35) for later use (step 750). Next, in order to eliminate the contribution in the power spectra from DC offset, a linear transform is applied to the data decontaminated of spikes and excursions but not eliminated due to saturation artifact (step 40 in FIG. 1). A Kaiser α=6.0 window appears to provide superior spectral resolution as compared to commonly used windows for EEG data processing, including Blackman, Cosine Taper, Boxcar or Hanning. The data is zero-padded and a 1,024 point fast Fourier transform (FFT) for determining discrete Fourier transforms is applied to generate power results.

Figure 7:
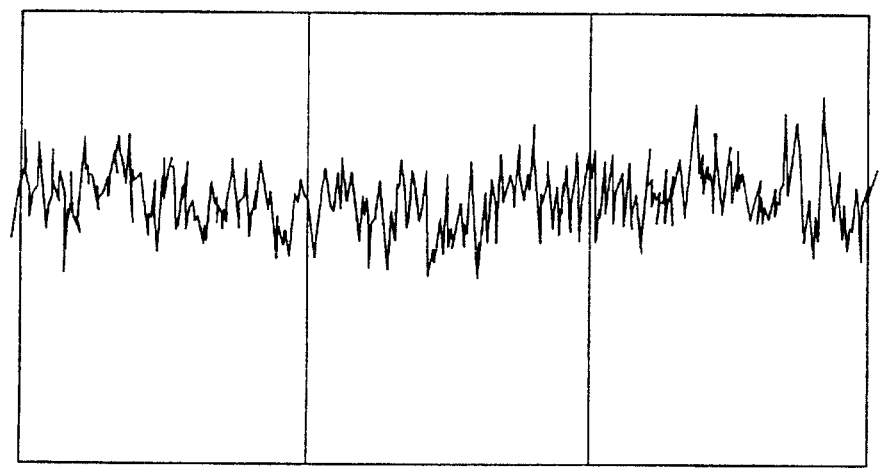
FIG. 7 is an EEG data schematic illustrating three overlaps generating a 50% overlapping window.

The absolute and relative (to the EEG band) power for all one hertz bins between 0 and 24 Hz, as well as the power and median frequencies for a number of frequency bands across the entire frequency range are computed (step 50). A 50% overlapping window is utilized to calculate the power for each epoch. FIG. 7 illustrates three overlapping epochs used to generate a 50% overlapping window of one second. This technique smooths the between-epoch power variations attributed to the non-stationarity of the EEG, improves the classification accuracy of the system, and reduces the number of epochs rejected for significant artifact. The results from the power and median frequency calculations are stored in temporary memory (step 55).

Next, epochs contaminated with high levels of electromyography ("EMG") can be identified and eliminated (step 60). The preferred embodiment contains this analysis. Although alternative embodiments need not contain it, misclassification errors can result if the data contains substantial EMG artifact. If this analysis is not performed, the method can continue with the next step, the identification and elimination of epochs with movement artifact (step 80). If the analysis is performed, the steps outlined in FIG. 3B are followed (step 70).

Figure 5A:
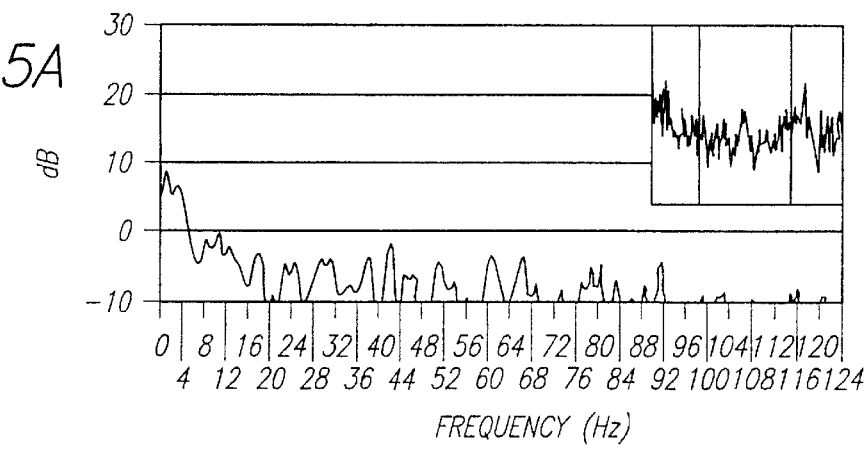
FIG. 5A is a graph depicting EEG data with low levels of EMG artifact.
Figure 5B:
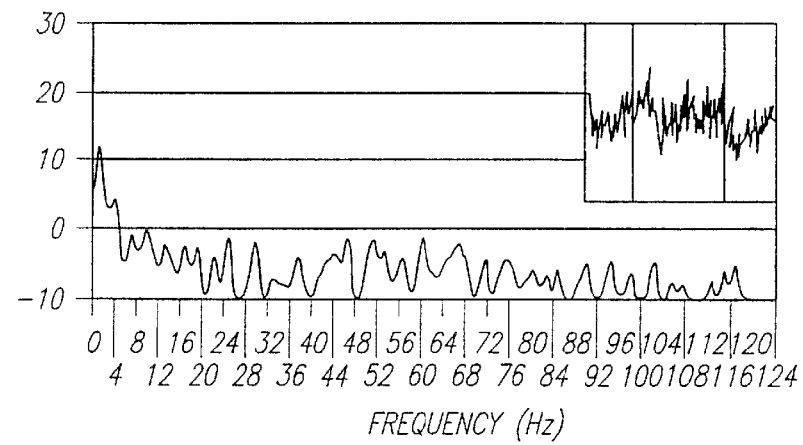
FIG. 5B is a graph depicting EEG data with medium levels of EMG artifact.
Figure 5C:
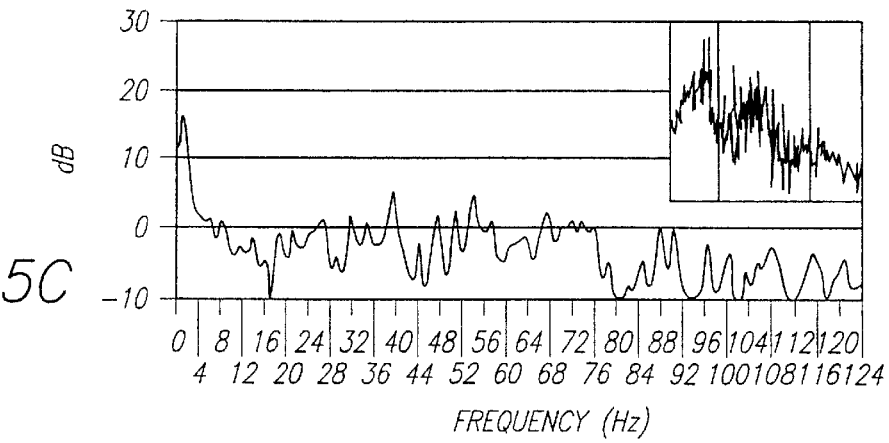
FIG. 5C is a graph depicting EEG data with high levels of EMG artifact.

Turning now in detail to FIG. 3B, first the power for the EEG band (the preferable range is 2.25 to 22.75 Hz for this procedure) and 10 Hz bands between 30 and 128 Hz for each overlap from the temporary memory of step 55 are retrieved (step 380). The power between 59 and 61 Hz should be avoided so that 60 Hz interference does not result in a misidentification of EMG artifact. Second, all variables are submitted to a stepwise analysis to determine the variables that are most predictive in identifying EMG artifact (step 385). Third, a DFA model is developed, using the predictive variables, to identify low, medium and high levels of EMG artifact in each overlap. Then the level of EMG artifact that results in a misclassification of the EEG signal by the classification model described in Section II is determined (i.e., significant EMG artifact) (step 390). Fourth, the number of overlaps that contain significant EMG is determined (step 400). FIGS. 5A through 5C illustrate EEG data with various levels of EMG artifact.

If significant EMG artifact is not determined in any of the overlaps, then the analysis of the data continues by returning to step 80 of FIG. 1 (step 410). If significant EMG artifact is identified in only one of three overlaps, the results for the two unaffected overlaps are averaged to represent the epoch (step 420) and the analysis of the data continues by returning to step 80 of FIG. 1 (step 410). On the other hand, if significant EMG artifact is identified in more than on overlap, the EMG counter is increased by one (step 430). Next, the EMG counter is read (step 440) and the subject is notified via an audio and/or visual alarm when the counter exceeds a certain threshold set to minimize the number of epochs rejected for EMG artifact (step 450). In any event, if significant EMG artifact is identified in more than one overlap, the epoch is rejected, the data is not processed (step 460), and the analysis starts from the beginning with the next epoch by returning to step 10 of FIG. 1 (step 470).

As an alternative method of identifying and eliminating epochs with EMG artifact, begin by retrieving the power between the 80 to 128 Hz band from step 55. If the power between 80 to 128 Hz is greater than or equal to 4.0 but less than 5.0, then classify the artifact as "Low." If the power is greater than or equal to 5.0 but less than 6.0, then classify the artifact as "Medium." If the power is greater than or equal to 6.0, then classify the artifact as "High." If significant EMG artifact is not determined in any of the overlaps, then the analysis of the data continues by returning to step 80 of FIG. 1 (step 410). If significant EMG artifact is identified in only one of three overlaps, the results for the two unaffected overlaps are averaged to represent the epoch (step 420) and the analysis of the data continues by returning to step 80 of FIG. 1 (step 410). On the other hand, if significant EMG artifact is identified in more than one overlap, the EMG counter is increased by one (step 430). Next, the EMG counter is read (step 440) and the subject is notified via an audio and/or visual alarm when the counter exceeds a certain threshold set to minimize the number of epochs rejected for EMG artifact (step 450).

Next, epochs that have not yet been eliminated but that are contaminated with high levels of movement artifact can be identified and eliminated (step 80). The preferred embodiment contains these procedures. Although alternative embodiments need not contain it, misclassification errors can result if the data contains substantial movement artifact. In any event, if these procedures are not performed, the method can continue with the next step, the identification of epochs with environmental electrical interference such as 60 Hz artifact (step 100). If the analysis is performed, the steps outlined in FIG. 3C are followed (step 90).

Movement artifacts, generally caused by sudden head or body movements or gross eye movements contribute to increased power in the slower EEG frequencies (i.e, below 3 Hz). FIG. 8A illustrates data contaminated with various levels of head or body movement artifact while FIG. 8B illustrates data contaminated with various levels of gross eye movement artifact. Because movement artifacts do not appear abruptly nor are isolated to a few data points, these artifact facts are not easily decontaminated. Rather, if the artifact is of sufficient magnitude that would result in a misclassification, the epoch should be rejected. Because movement artifacts are slow, the preferred method for identification and rejection of these artifacts is to analyze the three overlaps, which represent a one second epoch with a 50% overlapping window, in combination.

Turning now in detail to FIG. 3C, the power is first selected from the temporary memory of step 55 for the EEG band (the preferable range is 2.25 to 22.75 Hz for this procedure), 2 to 4 Hz band, 0 to 1.75 Hz band, and 1 Hz bins from 0 Hz to 5 Hz for each of the three overlaps (step 480). Next, the variables for the three overlaps of the one second epoch are submitted to a stepwise analysis to determine the variables that are most predictive (step 490). A discriminant function model is generated using the predictive variables to identify low, medium or high levels of movement artifact in the epoch and the level of movement artifact that results in misclassifications is determined (i.e., "significant" movement artifact) (step 500). Finally, a determination is made as to whether the epoch contains significant movement artifact (step 510).

If the epoch does not contain significant movement artifact, the analysis can continue with step 100 (FIG. 1B), with an identification of epochs with environmental electrical interference such as 60 Hz artifact (step 520). On the other hand, if the epoch does contain significant movement artifact, the movement counter is increased by one (step 530), the counter is read (step 540), and, if it exceeds a certain threshold set to minimize the number of epochs rejected for movement artifact, the subject is notified via an audio and/or visual alarm (step 550). Epochs containing significant movement artifact are rejected, the data is not processed any further (step 560), and the analysis resumes with the next epoch at step 10 of FIG. 1 (step 570).

An alternative method of identifying and eliminating epochs with significant movement artifact includes the following steps. First, select from the temporary memory of step 55 the power for the 2 to 4 Hz and the 0 to 1.75 Hz bands. If the power for the 2 to 4 Hz band divided by the power for the 0 to 1.75 Hz band is less than or equal to 1.05 and the power between 0 to 1.75 Hz divided by the power of the EEG band (the preferable range is 2.25 to 22.75 Hz for this procedure) is: (a) greater than or equal to 1.25 but less than 1.5, then classify the artifact as "Low"; (b) greater than or equal to 1.5 but less than 2.0, then classify the artifact as "Medium" or (c) greater than or equal to 2.0, then classify the artifact as "High." Then, determine the level of movement artifact that results in a misclassification of the EEG signal, reject all epochs with that level of artifact, increase the movement counter by one, notify the user if the counter exceeds a certain threshold, and resume the analysis with the next epoch.

Next, epochs that have not yet been eliminated but that are contaminated with environmental electrical interference can be identified (FIG. 1, step 100). The type of environmental electrical interference of concern is typically generated by a 60 Hz AC power source, but may also be other types of electrical interference that may exist in the environment, typically at frequencies below 128 Hz, such as may be generated by electrical equipment or electrically operated machinery. It should be apparent that the procedures described for identification of 60 Hz interference can also be readily adapted by those skilled in the art to identify such other types of environmental electrical interference.

Since environmental electrical interference such as 60 Hz interference can be readily isolated and eliminated in the frequency domain, epochs contaminated with this artifact do not necessarily need to be rejected. An increase in the power between 59 to 61 Hz, however, is highly correlated with increasing scalp-electrode impedances and suggests an electrode needs to be checked (i.e., problematic electrode). The preferred embodiment incorporates impedance-checking hardware, programmed to perform routine impedance testing (e.g., every 15 minutes) of the electrodes. In addition, the level of 60 Hz interference can be monitored to initiate immediate impedance checking. Alternative embodiments could rely solely on the magnitude and duration of 60 Hz interference to determine when an electrode may need to be checked. Yet other alternative embodiments need not monitor for 60 Hz interference altogether. In any event, if this analysis is not performed, the method can continue with the next step (step 120). If the analysis is performed, the method continues with step 110 proceeding to the steps outlined in FIG. 3D.

Turning now in detail to FIG. 3D, the power between 59 to 61 Hz and the power between 2.25 to 22.75 Hz is first selected from the temporary memory of step 55 (step 580). A Power Ratio (PR) is calculated by dividing the power between 59 to 61 Hz by the power of the EEG band (the preferable range is 2.25 to 22.75 Hz for this procedure) (step 590). The power ratio is then analyzed to determine the level of 60 Hz artifact present (step 600). A ratio greater than or equal to 0.55 but less than 0.70 is categorized as "Low" (step 610). A ratio greater than or equal to 0.70 but less than 0.90 is categorized as "Medium" (step 620). A ratio greater than or equal to 0.90 is categorized as "High" (step 630). If the level of 60 Hz artifact is "High" the 60 Hz counter is increased by one (step 640). The counter is then read (step 650), and, if it exceeds a certain threshold for any electrode and on-line impedance checking is available, the impedance of the electrode corresponding with the "High" artifact should be measured (step 654). If the impedance value exceeds a certain threshold, the subject is notified via an audio and/or visual alarm to fix the problematic electrode (step 656). Alternatively, if on-line impedance checking is not available, the counter is read (step 650) and, if the counter exceeds a certain threshold set to recognize a problematic electrode, the subject is notified via an audio or visual alarm to check the electrode (step 660). In any event, the epoch is not rejected, and the analysis continues with step 120 of FIG. 1 (step 670). In an alternative embodiment, epochs with high levels of 60 Hz artifact can be eliminated, in which case the analysis would resume with the next epoch and step 10 of FIG. 1.

As described above, in the preferred embodiment, the foregoing analysis is performed in real time. Likewise, in the preferred embodiment, the subsequent analysis described below is performed in real time. However, at this point, the data that has not been rejected yet may also be stored for future off-line analysis (step 130). If this is done, the off-line analysis can also follow the same steps described herein below for the preferred embodiment.

C. Identification and Decontamination of Eye Blinks

Figure 9:
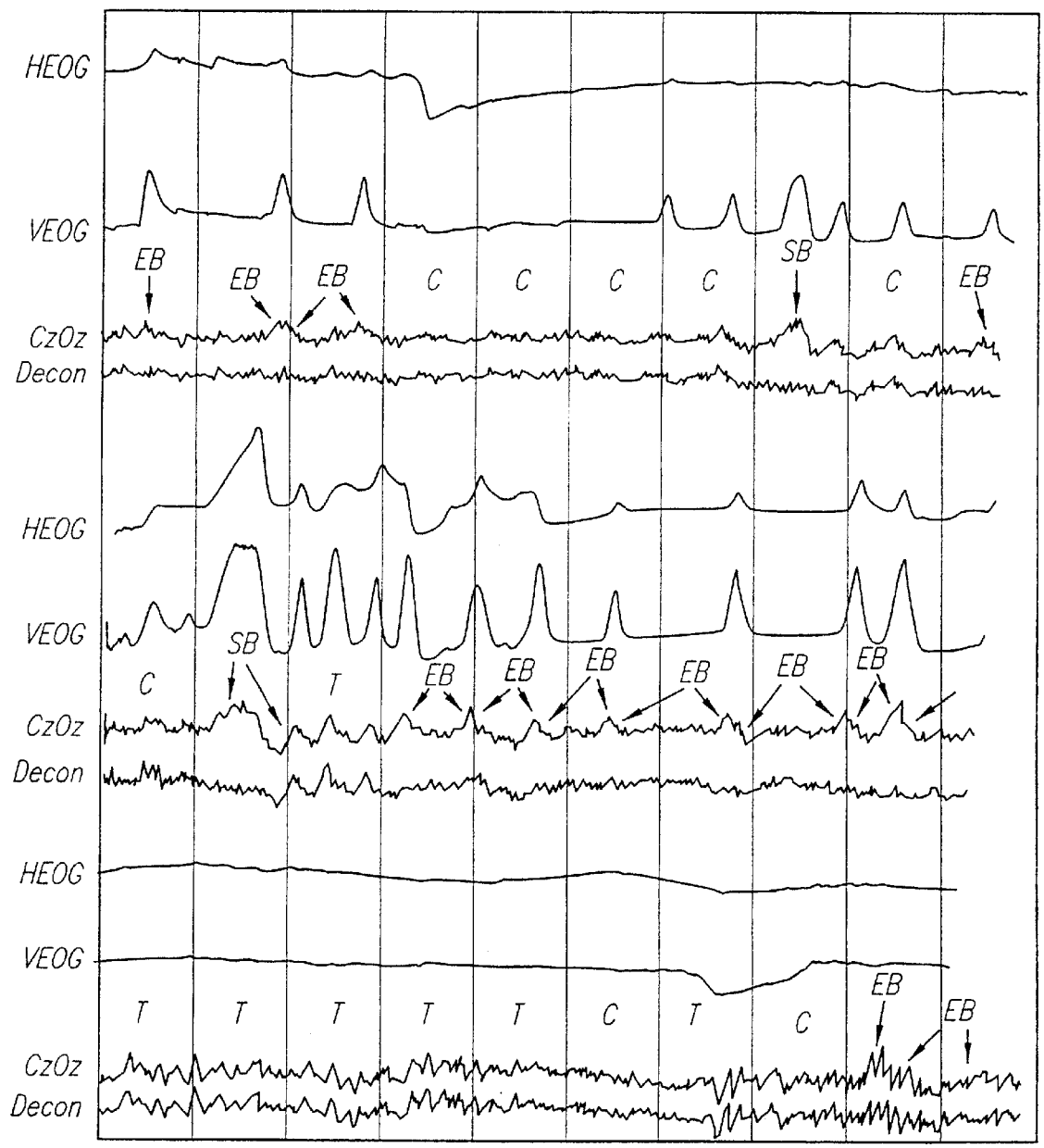
FIG. 9 is a graph depicting EEG data (ten, one second epochs) in the time domain with eye blinks, and after decontamination of the eve blinks. Epochs classified with: theta waves are labeled "T," fast blinks are labeled "EB," slow blinks are labeled "SB," and non-eye blink controls are labeled "C." EOG recordings are presented for verification.

For the data that has not yet been eliminated, eye artifacts can next be identified and decontaminated (step 140). FIG. 9 is a chart illustrating EEG data with eye artifacts, and EEG data following decontamination of these eye artifacts. The preferred embodiment contains this analysis. Although alternative embodiments need not contain it, misclassification errors can result if the data contains substantial eye artifact. In any event, if this analysis is not performed, the method continues with the next step 160, the classification of alertness along the alertness-drowsiness continuum. If the analysis is performed, in the preferred embodiment, the method continues to step 150 and proceeds to the steps outlined in FIG. 2.

The preferred embodiment monitors the EEG and classifies alertness along the alertness-drowsiness continuum without the use of simultaneous EOG recordings. Accordingly, eye artifacts are identified and decontaminated using only the EEG recordings. Because the method of the preferred embodiment employs a 50% overlapping window for calculating the power for each one second epoch, the procedures to identify and decontaminate eye blinks across the three overlaps should be sensitive to eye blinks occurring in the center of an overlap as well as eye-blinks located partially between two contiguous overlaps and/or epochs (hereafter referred to as "partials"). FIG. 7 illustrates the three overlaps of an EEG signal, which are averaged when a 50% overlapping window is applied.

1. Identification of Eye blinks

The analysis begins with the data in the frequency domain for epochs that have not been previously eliminated. First, the absolute and relative power for one Hz bins between 1 Hz and 24 Hz, the EEG band (the preferable range is between 2.25 Hz and 22.75 Hz for this procedure), and median frequencies for the alpha, EEG and 2 to 128 Hz bands are selected from the temporary memory of step 55 in FIG. 1 (step 210).

Next, or in parallel with step 210, data still in the time domain from the temporary memory of step 35 is retrieved (step 220), and then passed through a 7 Hz low pass IRR filter (step 230). Cross-correlation variables are computed for each of the three overlaps that comprise a 50% overlapping one second epoch, using a 0.375 second, 40 $\mu$V sine wave (step 240).

The present inventors have determined that a 0.375 second (96 data points) 40 $\mu$V sine wave is the optimum eye blink identification shape when used to compute the cross-correlation variables of Table 1, and that a 7 Hz lowpass filter provides the best identification accuracy. Using a discriminant function developed with over 450 one second epochs, the inventors determined that each epoch should be categorized into one of four groups: (a) fast-blinks ("EB") (0.25 to 0.5 seconds), (b) slow-blinks ("SB") (0.5 to 1.0 seconds), (c) EEG theta activity ("T"), and (d) EEG controls with no artifacts or theta activity ("C") (see FIG. 9 for an illustration). Approximately 25% of the epochs used to develop groups (a) and (b) include eye blinks located near the edge of the overlap/epoch or located partially between two contiguous overlaps/epochs. Data for group (c) include epochs 2 to 5 seconds subsequent to the onset of sleep which reflect a mixed alpha/theta signal, or predominant theta waves.

The power variables of step 210 and the cross-correlation variables of step 240 are then submitted to a discriminant function analysis ("DFA") for classification in one of the four groups described above (step 50). There are two approaches which may be employed using DFA to identify eye blinks in the three overlaps that constitute a one second epoch. The preferred method ("Method 1"), trains a DFA model using the variables derived from a single overlap to identify all eye blinks in that overlap. The eye blinks in each overlap are then decontaminated prior to averaging of the three overlaps. The alternative method ("Method 2") trains a DFA model using variables derived from all three overlaps to identify all eye blinks in the epoch. For either method, procedures are applied, as described below, to determine when two overlaps identify the same eye blink and ensure eye blinks are decontaminated for all overlaps. The description in section 2. below pertains to Method 2. However, it will be obvious to one skilled in the art that with minor modifications the procedure described can also be applied to Method 1. Sections 3 and 4 apply to both Methods 1 and 2.

Hence, if Method 1 or 2 is used, a stepwise analysis is used to select the variables from those listed in Table 1 that the inventors found to be most predictive in identifying eye blinks and classifying epochs into the four groups. Analyzing the 450 epochs used for development of the classification model, the DFA for Method 2 provided a false negative rate of 8.9% for fast and slow blinks, a false positive rate of 4.7% for theta and controls, with an overall classification accuracy of 93.3%.

TABLE 1

| Variable Name | Description of Variable |
|---|---|
| CCR | Maximum normalized cross correlation value in the epoch (1-sec overlap) |
| CCV | Maximum cross correlation value in the epoch |
| LCCV | Log base 10 of CCV |
| PEP | Power of potential eye blink at the point of maximum correlation determined by cross correlation function. |
| ET | Power of potential eye blink at the point of maximum correlation normalized to the total cross correlation power of the epoch |
| LET | Logbase 10 of ET |
| PSH | Power of eye blink identification at point of maximum correlation |
| ST | Power of the eye blink identification shape at point of |

TABLE 1-continued

| Variable Name | Description of Variable |
|---|---|
| | maximum correlation normalized to the cross-correlation power of the eye blink identification shape |
| NAD | Number of additional places (maximum of six) where cross correlation function identified potential eye blinks with correlation value >= 25% of the maximum correlation value |
| CCO | Location of maximum correlation between blink and (data point) relative to beginning of the epoch |
| Offset | Location of peak of potential eye blink relative to beginning of the epoch |
| PA0 | Minimum power of all NAD values |
| PA1 | Maximum power of all NAD values |
| PA2 | Summation of power for all NAD values |
| PA3 | Mean power across all NAD values (PA2 divided by number of NADs) |
| LPA0 | Log base 10 of PA0 |
| LPA1 | Log base 10 of PA1 |
| LPA2 | Log base 10 of PA2 |
| LPA3 | Log base 10 of PA3 |
| OA2 | Mean CCO for NAD values |
| Power of EEG band | Power from 2.25–22.75 Hz |
| Absolute bin power | Power for one-HZ bins from 1 to 12 Hz |
| Relative power | Power for one-Hz bins from 1 to 12 Hz divided by the power for the EEG band (2.25–22.75 Hz) |

2. Identification of the Peak of the Eye Blink

After epochs with eye blinks have been identified and classified by the DFA as either fast blinks (EB) or slow blinks (SB) (step 255), the location of the eye blink within an epoch is then identified (Step 260). The optimum peak location (i.e., the location of the peak of a potential eye blink relative to the beginning of the epoch) is determined based on the power of the potential eye blink at the point of maximum correlation as determined by the cross-correlation function (PEP in Table 1) and the power of the eye blink identification shape at the point of maximum correlation normalized to the cross-correlation power of the eye blink identification shape (ST in Table 1). Consideration must be given as to whether two overlaps identify the same eye blink, and as to the size of the eye blink.

Specifically, the following rules are applied to determine the peak of the eye blink after the DFA has determined that an overlap or an epoch contains an eye blink.

a) When two overlaps identify the same eye blink:
  (1) The point of maximum correlation for the two overlaps (i.e., left and center and right) should be within ±8 data points. If the Offset for overlap 0 (Left) (or overlap 2 (right)) and the Offset for overlap 1 (center are within 8 data points, then apply the following rules to determine optimum peak location:
    (a) If the PEP for overlaps 1 and 0 (or 2) are <40, then ignore the DFA eye blink classification.
    (b) If ST=1 and PEP<=40 for overlap 1, then the peak is located at Offset 1.
    (c) If ST=1 and PEP>=40 for overlap 0 (or 2), then the peak is located at Offset 0 (or 2).
    (d) If ST=1 and PEP>=40 for overlaps 1 or 0 (or 2); and the PEP for overlap 1>PEP for overlap 0 (or 2) or the PEP for overlap 1=the PEP for overlap 0 (or 2) then the peak is located at the Offset for overlap 1, otherwise the peak is located at the Offset for overlap 0 (or 2).

b) Identification of eye blinks in a third overlap when two of the overlaps identify the same eye blink(s):
  (1) If ST=1 for the third overlap 0 (or 2) and the PEP for the third overlap 0 (or 2) is: (a) >=50% of PEP that satisfies Rule I.C.2.a), and
    (b) >=40, then the peak of an additional eye blink is located in the third overlap at Offset 0 (or 2).
  (2) If ST>=0.95 for the third overlap 0 (or 2) and the PEP for the third overlap is: (a) >=65% of the PEP that satisfies Rule I.C.2.a), and
    (b) >=40, then the peak of an additional eye blink is located in the third overlap at Offset 0 (or 2).

c) Identification of eye blinks when Rule I.C.2.a) has not been met:
  (1) If more than one overlap has ST=1 and PEP>40, then the Offset of the overlay with greatest PEP (0, 1 or 2) should be used to locate the peak of the eye blink.
  (2) After applying I.C.2.c)(1), if PEP of a potential eye blink in the second or third overlap >40 and >=50% of the overlap with the greatest PEP, then the Offset of the second or third overlap should be used to locate the peak of the additional eye blink(s).
  (3) If only one overlap has ST=1 and PEP>40, then the eye blink is located at the Offset for that overlap.
  (4) If no overlap has ST=1, then the overlap with the greatest PEP which is >40 is the location of the peak of an eye blink.

d) Identification of very large eye blinks:
  (1) If any overlap has ST>=0.65 with a PEP 200% greater than the PEP of the eye blink(s) identified with rules I.C.2.a) through I.C.2.c), then the Offset for that overlap is the location of the peak(s) for an additional eye blink(s).

3. Identification of the Beginning and Ending of each Eye Blink

The beginning and ending data point of each eye blink is determined (step 265) through the implementation of a number of steps. First, the maximum data point of the eye blink is first identified by evaluating 32 data points to the left and the right from the point identified by cross correlation as the point of maximum correlation. The data point within the 64 data point span with the maximum amplitude is the peak of the eye blink (H0). Next, the data points to the left (right) of the peak of the eye blink that form additional peaks are identified. Additional peaks are determined when data point (s) to the left and right of the peak of the eye blink have amplitudes less than the peak. (The additional peaks can be labeled sequentially beginning with H1, H2, etc.) Then, the data points to the left (right) of the peak of the eye blink that form a trough are identified. Troughs are determined when data point(s) to the left and right of the trough have amplitudes less than the trough. (The troughs can be labeled sequentially beginning with L1, L2, etc.) Finally, the slopes between the first trough (L1) and second Trough (L2) (labeled SLL1), and between the second trough (L2) and the third through (L3) (labeled SLL2), and so on, are computed.

Next the filtered data are analyzed to identify the preliminary beginning (P-begin) and ending (P-end) data points of each eye blink. To do so, the peak of the eye blink for slow eye blinks is first adjusted when the data point of maximum amplitude is greater than 32 data points away from the point of maximum correlation, as identified above by cross correlation. If any of the peaks located as described above and identified as H1 et seq. are greater than the peak identified above as H0 (i.e., H1>H0), then the peak with the greatest amplitude should be designated as the peak of the eye blink (i.e., H1 renamed as H0) and all peaks, troughs and slopes relabeled accordingly.

On occasion, eye blink and brainwave signals become mixed, resulting in a disruption of the smooth parabolic shape of the eye blink. When this occurs, the beginning (end) of the eye blink can be prematurely identified. If the amplitude of L1, L2 and H2 are within ±1 $\mu$V compared to H1 (or the amplitude of L2, L3 and H3 are within ±1 $\mu$V compared to H2, etc.) then SLL1 should be computed between L1 and the first trough (e.g., L3, etc.) that breaks out of the ±1 $\mu$V range, SLL2 should then be computed between L3 and L4, providing these data points exceed the ±1 $\mu$V range, etc.

The P-begin (P-end) of an eye blink is the trough closest to the peak of the eye blink (L1) when either: (a) the slope between the two troughs closest to the peak of the eye blink is <0.30 (i.e., beginning with SLL1); or (b) the amplitude between the first trough (L1) and the first additional peak (H1) is >40% if the amplitude of the peak of the eye blink (i.e., [(the amplitude of the first additional peak (H1)–the amplitude of the first trough (L1))/[the amplitude of the peak of the eye blink]>0.40). Otherwise, if either of these two conditions have been met for SLL1 or H1 and L1, then continue applying the algorithm (i.e., SLL2, H2 and L2, etc.). For slow eye blinks, the first two conditions, (a) or (b), may be prematurely met (due to mixed brainwave and eye blink signals). If the amplitude of the P-begin (P-end) of the eye blink is greater than 50% of the amplitude of the peak of the eye blink, then continue applying the rules of this paragraph until this condition is met (i.e., L1≦H0×0.5).

For fast eye blinks, the amplitudes at the beginning and end of an eye blink are approximately the same. If the absolute value of the slope between the P-begin and P-end of the eye blink ≧40, then continue applying the rules described in the previous paragraph (i.e., [amplitude at P-end of eye-blink–amplitude at P-begin of eye blink)/the number of data points between P-begin and P-end of the eye blink]≧0.40).

As an optional enhancement, the beginning and end points of the eye blink can be trimmed to accommodate the effects from mixed brainwave and eye blink signals. To do so, the point when the shape of an eye blink changes from rapidly falling to a tapering transition to the end of the eye blink (transition point) is identified. To that end, the slope between the peak of the eye blink and P-begin (P-end) of the eye blink is computed; and the angle of the slope is maintained while the line is shifted toward the center of the eye blink until the line touches the last data point of the eye blink. The point of last contact is the transition point. Next, a line is extended from the peak of the eye blink through the transition point to the data point that has the same amplitude as P-begin (P-end) to identify the trimmed beginning (T-begin) and trimmed end (T-end) of the eye blink. If the difference between P-begin (P-end) and T-begin (T-end) is greater than 10 data points then T-begin (T-end) is the start (end) of the eye blink; otherwise, P-begin (P-end) is the start (end) of the eye blink.

Finally, the data points corresponding with the beginning and end of the filtered eye blink are shifted back in time (e.g., approximately 22 data points for 7 Hz IRR lowpass filter) to identify the beginning and end of the eye blink in the unfiltered data.

4. Decontamination of Eye Blinks

After eye blinks are identified, the amplitude of the filtered eye blink should be decontaminated from the unfiltered EGG signal. To reduce the computational demands of decontamination for real-time processing, the data previously filtered for identification of eye blinks should be used. The inventors determined that the use of a 7 Hz filter for the decontamination process, however, occasionally results in decontamination of EEG in the theta and alpha bands.

Prior to decontamination, eye blinks that require shape fitting are first identified (step 267). When the brainwave and eye blink signals are mixed, a parabolic curve is fitted to the shape of a filtered eye blink. When H1 has a greater amplitude than H0, and H1 is more than 32 data points away from H0, then the top of the eye blink requires shape fitting. When any of the rules described in I.C.3.b) are violated, the side(s) of the eye blink requires shape fitting.

To implement shape fitting (step 270), a sufficient number of data points need to be selected in order to fit a parabola over the eye blink. Then the data points of the parabola which correspond with the affected region of the eye blink are used to replace the data points of the affected region of the eye blink. The amplitude of the filtered (and, when appropriate, fitted) eye blink is then subtracted from the unfiltered EEG signal (step 275). An adjustment to the amplitude of the filtered eye blink may be required to provide a smooth transition in the unfiltered data after decontamination of the eye blink. To that end, the amplitude of the data points corresponding with the beginning and end of the filtered eye blink are determined. Then, the slope between the data points corresponding with the beginning and end of the filtered eye blink is computed. An "adjusting amplitude" is calculated by subtracting the amplitude of the slope line (between the beginning and end of the filtered eye blink) from the amplitude of the filtered eye blink for each data point of the eye blink. Finally, the adjusting amplitude is subtracted from the corresponding unfiltered data point.

5. Computation of Power Spectra and Median Frequencies

Finally, after the eye blinks have been decontaminated the power between 1 Hz and 9 Hz and the EEG bands (preferably the 2.25 to 17.75 Hz for the classification model described below) are recomputed, as well as the median frequencies for the alpha (preferably 8 Hz to 13 Hz), EEG, and 2 Hz to 128 Hz bands (step 280). If the procedures to identify and decontaminate eye blinks are not applied or eye blinks are not detected, the power and median frequencies computed in step 55 are retrieved (step 210). Hence, the power and the median frequencies, either from step 210 or step 280 (step 290), are used as inputs later on for further classification of the EEG in the frequency domain (step 295).

6. Alternative Embodiments

In an alternative embodiment, the data need not be decontaminated of eye blink artifact. However, it is possible that contaminated data will result in a higher rate of misclassification along the alertness-drowsiness continuum. In another alternative embodiment, epochs with eye artifacts can be completely eliminated. However, this alternative has the potential of eliminating an excessive amount of data.

In yet another alternative embodiment, eye blinks can be identified with the addition of eye monitors, and then the contaminated data treated in any of the various means described above. Finally, eye blinks can be identified by employing a time series analysis. This analysis, described hereinbelow, classifies each epoch along the alertness-drowsiness continuum, and, by comparing it to the classification of a sequence of preceding (for real-time analysis) and/or subsequent (for off-line analysis) epochs, determines whether an eye blink is present. If an eye blink is found, the data can be treated in any of the various means described above.

II. Calculation of State of Alertness

Figure 4B:
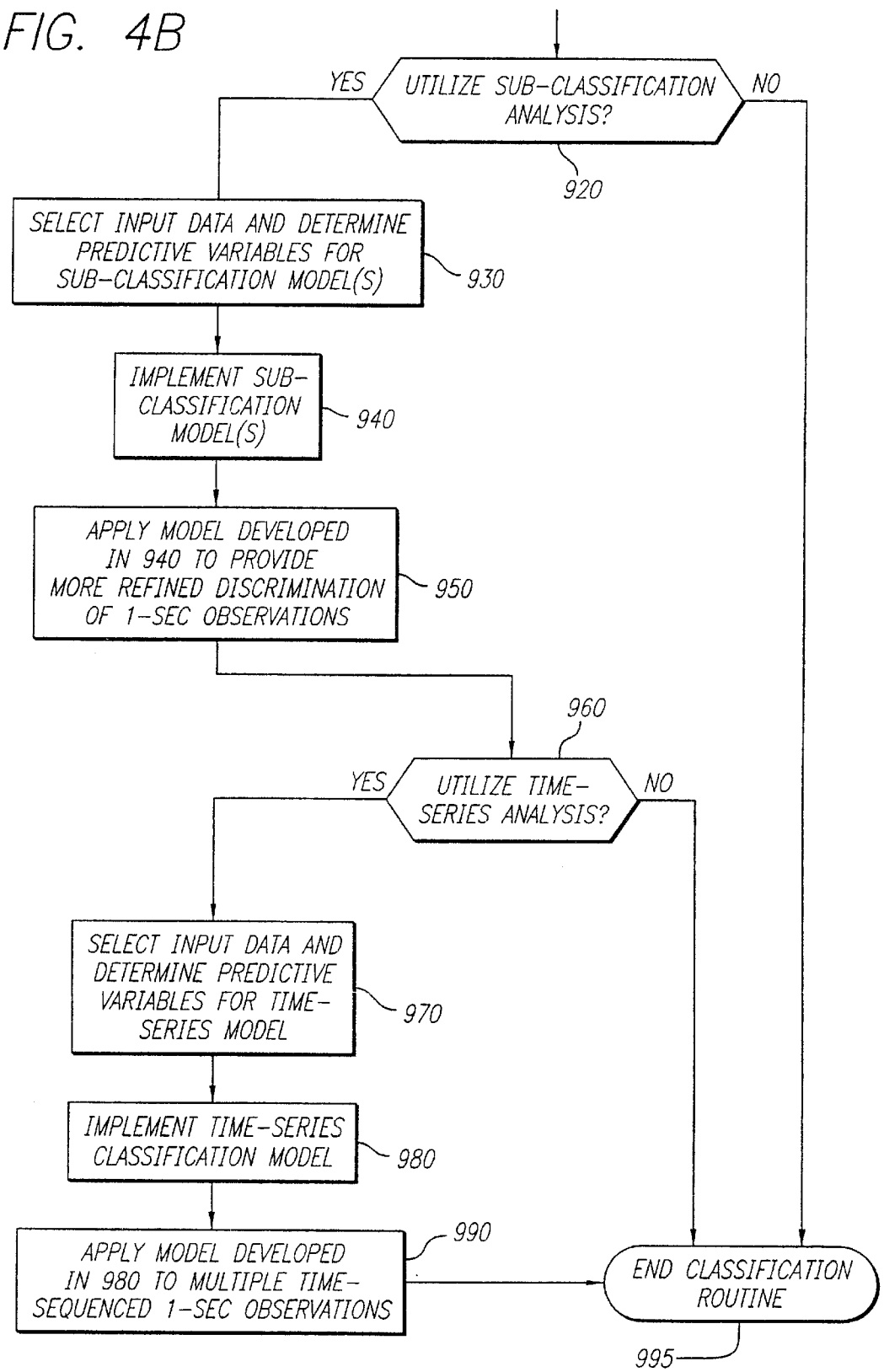

Returning now to FIG. 1B, after the data is acquired and prepared to reduce the potential for misclassifications, the subject's state of alertness along the alertness-drowsiness continuum can be monitored and analyzed based on one or multiple, one-second epochs free of artifact (step 160). The specific steps are detailed in FIG. 4A and FIG. 4B. To begin with, a classification model is developed based on a selected number of subjects. A classification model requires two inputs: data selected to represent and train the model to identify specific output classes, and transformations of the data which provide the model the optimal discrimination capabilities. The preferred classification model employs discriminant function analysis (DFA). However, it will be apparent to one skilled in the art that neural network analysis or other linear or non-linear statistical analyses using categorical variables can also be used.

A classification model can be developed to classify input data into distinct output classes (Section II.B.1). Alternatively, univariate or multivariate distance measures (e.g., "Mahalanobis Distance") or number of standard deviations from the output class mean ("centroid") can be used for classification of input data (Section II.B.2.). Classification models can also be developed for multiple databases (Section II.A) and/or fitted for each new subject (Section II.C and II.D) in order to overcome between-subject variability and provide optimal classification accuracy. Finally, classification models can be developed using a unilevel approach or a multi-level approach (Section II.E).

A. Grouping of Subjects with Similar EEG Characteristics

Turning in detail to FIG. 4, in the preferred embodiment, quantification of the subject's state of alertness along the alertness-drowsiness continuum begins with artifact-free EEG variables (step 800). However, in alternative embodiments, the data analyzed might contain various artifacts. Depending on the type and level of artifact, contaminated data might result in a higher level of misclassification.

The preferred embodiment, furthermore, utilizes multiple databases with corresponding classification models in order to reduce the effects of variability across subjects. Alternative embodiments can utilize only one database, in which case the data is not assigned to various databases, and is used to determine predictive variables for each classification model. If multiple databases are utilized, however, subjects with similar EEG characteristics are grouped into various databases using cluster analysis to assign Cluster Groups. This enables an individual's EEG to be profiled during each of a number of baseline conditions and to be placed in one of a finite number of Cluster Groups. Patterns in the Cluster Group assignments across the baseline conditions are then used to identify and select database membership. Alternatively, a cluster analysis that uses data from all of the baseline conditions can assign database membership.

The inventors determined that the approach that analyzes the patterns of the Cluster Group assignments provided better grouping of subjects with similar EEG characteristics than using the cluster analysis to assign database membership directly. For the preferred configuration, three baseline conditions were selected to predict membership into one of three databases. The number of baseline conditions, as well as the number of databases, could be adjusted in an alternative configuration. Determining the Cluster Groups for the baseline conditions is necessary for implementation of the fitting procedures described below.

1. The following procedure can be implemented to classify Cluster Groups by using cluster analysis (step 820).
    a. Select artifact free EEG recordings under the following conditions:
        1) During a mental performance task (i.e., reaction time, cognitive or memory task).
        2) While sitting quietly with eyes open looking straight ahead.
        3) While sitting quietly with eyes closed.
        4) While the subject is sleep deprived at the point when the individual is no longer responding to a simple behavioral task and sleep onset has occurred.
    b. Compute the mean and standard deviations for each predictive variable (i.e., power of 1 Hz bins, power of EEG band, median frequency of EEG bands, etc.) for the artifact free data derived previously by individual.
    c. Compute the means and standard deviation for each predictive variable derived above across individuals.
    d. Determining the Z-score for each predictive variable derived in Step c. by subtracting the population mean (step c.) from the individual's mean (step b.) and dividing by the population standard deviation (step c.).
    e. Submitting the data derived in Step d. to cluster analysis.

2. Next, analyze the patterns of the Cluster Group assignments across individuals and baseline conditions to group individuals with similar EEG characteristics into a common database (See examples shown in Table 2) (step 830).

TABLE 2

| | Cluster Group Assignment | | |
| --- | --- | --- | --- |
| | High-Vigilance | Low-Vigilance | Eyes-Closed |
| DataBase 1 | 2 | 2 | 3 |
| | 2 | 2 | 2 |
| | 3 | 2 | 3 |
| DataBase 2 | 3 | 3 | 4 |
| | 1 | 3 | 3 |
| | 2 | 3 | 3 |
| | 3 | 3 | 3 |
| | 4 | 4 | 4 |
| | 4 | 3 | 4 |
| DataBase 3 | 1 | 1 | 3 |
| | 1 | 1 | 3 |
| | 1 | 1 | 2 |
| | 1 | 1 | 1 |

Figure 10:
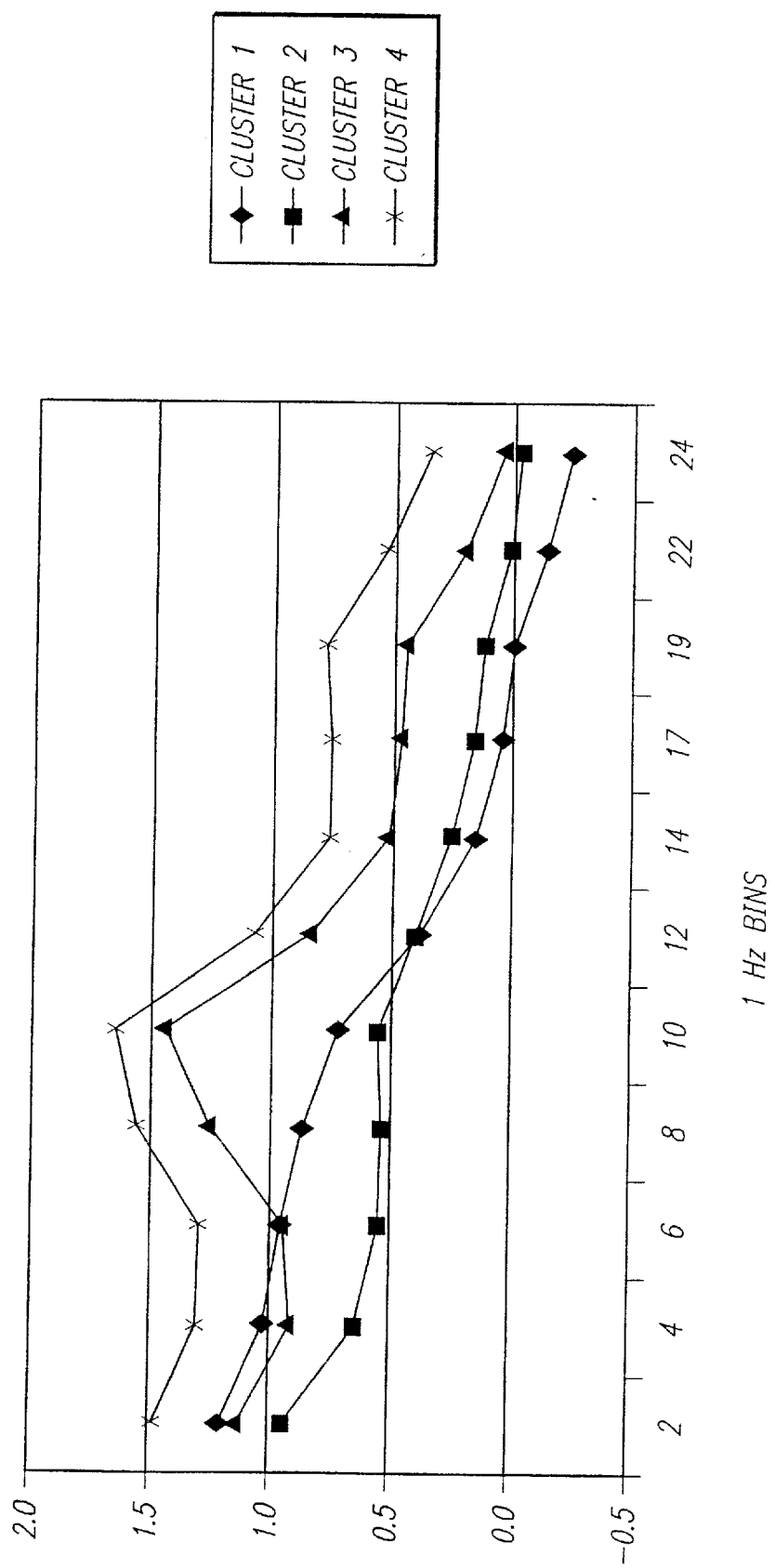
FIG. 10 is a graph depicting the mean power of 1 Hz bins for four cluster groups. Cluster 4 displays greater overall power in each bin compared to the other clusters. Clusters 3 and 4 exhibit similar patterns in the distribution or power across the 1 Hz bins, except for 10 to 14 Hz. Cluster 2 exhibits suppressed power in the S to 12 Hz range and increased power in the 22 and 24 Hz bins, compared to Clusters 3 and 4. Cluster 1 exhibits substantially greater overall power from 2 to 12 Hz compared to Cluster 2 and less power above 12 Hz.

3. By way of explanation, FIG. 10 provides a graphic representation of the mean logged power of the predictive 1 Hz bins for CzOz for the Cluster Groups that are used to assign database membership. These Cluster Groups can be described as follows:
    a. Cluster Group 1—proportionately greater power in the 2 to Hz, with relatively less power above 10 Hz. Higher amplitude signals commonly depict the EEG profile during sleep. Subjects with very large heads tend to exhibit low amplitude signals with relatively low alpha and beta power and clearly defined low amplitude theta waves during the baseline conditions.
    b. Cluster Group 2—relatively low power across most EEG bins and increased power in the 22 and 24 Hz bins.
    c. Cluster Group 3—increased power in most EEG bins, more evident between 6 to 12 Hz and a drop off in power in the 22 and 24 Hz bins.
    d. Cluster Group 4—relatively high power across all EEG bins, similar distribution of relative power across 1 Hz bins as Cluster Group 3 except a slight decrease in the 10 to 14 Hz bins.

4. After each database has been developed and profiles have been identified, the data required to develop the classification model(s) (i.e., input data selected for each class and predictive variables) can be separated to develop a classification model for each database (Step 840).

B. Design Generalized Classification Model

Two approaches can be implemented to provide a generalized classification model. These approaches can be used at the appropriate time, when called for, as described in the various sections below. The common element between the two models is the selection of the input data used to train the classification output classes (step 840).

1. Selection of classes/categories—The classes or categories selected for the classification model need to be representative of or provide the capability to classify the entire alertness continuum:
   a. To classify the state of alertness for the EEG along the alertness-drowsiness continuum, a minimum number of classes should be established with data preferably acquired during:
      1) A reaction time, memory or cognitive task ("mental performance task") with subjects fully rested in order to characterize a highly alert/vigilant condition ("High Vigilance").
      2) A non-specific task, such as sitting quietly, with subjects fully rested to characterize a low vigilance condition. When the EEG is categorized into this group, although fully rested, subjects might be daydreaming or not paying a high degree of attention ("Low Vigilance").
      3) Sleep deprivation, to characterize a fatigued state which might result in performance errors, etc. ("Awake—sleep deprived").
      4) The transition to sleep onset with subjects who are sleep deprived to identify both the momentary lapses in the awake state (i.e., eyes close for 1 to 2 seconds) and sleep onset (i.e., eyes remain closed for more than 5 seconds ("Sleep").
   b. Additional classes that are useful in providing more discrete classification of the subject's alertness state can be established, as necessary, with data acquired during:
      1) A reaction time, memory or cognitive task ("mental performance task") with subjects sleep deprived and making performance errors. This state is useful in identifying awake conditions when the subject poses a risk to themselves or others, depending on the task they are currently undertaking (i.e., operating a vehicle, heavy equipment, or monitoring an aviation radar screen). It is not critical that the classification model identifies this state as unique from other low vigilance states (i.e., the non-specific fully rested task (see 1.b above)). Rather, the objective is to identify the output classes that put the subject at risk under certain conditions.
      2) A non-specific task with eyes closed. Since subjects do not have their eyes closed during activities of daily living (i.e., at work, driving a vehicle, etc.), this class does not naturally fit along the alertness-drowsiness continuum. The Eyes Closed state, however, is highly predictive of the onset of sleep. Optimally two Eyes Closed classes should be developed from fully rested and sleep deprived sessions to provide further discrimination ("Eyes Closed—Fully Rested and Eyes Closed—Sleep Deprived).

2. Implementing the Classification Model—Two approaches can be employed to implement a generalized classification model.
   a. In the first approach for implementing a classification model, the steps below classify input data into a distinct output class. The limitation of this model is that it chooses a single outcome (winner) and does not distinguish between observations that clearly belong to a single output class from those that fall on the border between two classes.
      1) Select data acquired under specific conditions and/or with specific characteristics to train the DFA to identify the selected classes/categories (as explained above in Section II.B.1. (step 840).
      2) Compute the variables that may be useful in characterizing the observation and assign an input class to the observation (step 840 continued).
      3) Apply a stepwise procedure to identify the variables that are most predictive in classifying the training data into their respective input classes (step 840 continued).
      4) Compute the mean values ("centroids") which correspond with each input class (step 850).
      5) Apply the discriminant function procedure to generate one constant and coefficients for each of the predictive variables ("coefficients"), for each of the output classes (step 870).
      6) To classify an observation, compute the DFn's for all classes by adding the constant to the sum of all of the coefficients multiplied by the variable values (e.g., power for the 8-Hz bin for the observation, etc.) (step 910).
      7) Compare the DFn's computed in step 6) to determine the output class of the observation. The observation is generally assigned the output class/category based on the DFn with the largest (or smallest, depending on the calculations made in step 6) value (step 910 continued).
   b. A complementary or alternative method can be implemented to generate a measurement based on univariate or multi-variate distance (e.g., Mahalanobis Distance) or number of standard deviations (e.g., Z-score) the observation is from the output class mean ("Centroid"). This approach, used in combination with the first method, could determine whether an observation clearly belongs to a single output class (i.e., small distance measure) or falls on the border between two classes (i.e., large distance measures from the centroids of both classes). Rules could also be developed to assign an output class for an observation based on the distance measure. To implement the distance measure classification model:
      1) Select data acquired under specific conditions and/or with specific characteristics to train the DFA to identify the selected classes/categories.
      2) Compute the variables that may be useful in characterizing the observation and assign an input class to the observation.
      3) Apply a stepwise procedure to identify the variables which are most predictive in classifying the training data into their respective input classes.
      4) Compute the mean values ("centroids") which correspond with each input class.
      5) Apply the discriminant function procedure to the centroids to generate one constant and coefficients for each of the predictive variables ("coefficients") for each of the output classes.
      6) Apply the coefficients derived in step 5) to the training data and determine the centroids for each class.
      7) Generate a distance measurement indicating how far the observation is from the centroid, for each observation.
      8) Establish parameters for distance measurements which correspond with the input classes.
      9) Utilize steps 7) and 8) to assign an output class to an observation or assess the degree of similarity between an observation and a centroid.

C. Assign Database Membership for New Subjects

Section II.B. above explains how to develop the procedures to identify multiple databases and generate multiple classification models for each database. When multiple databases are used, subjects need to be assigned to the database which best fits their EEG profile (step 860). To do so, the following steps can be implemented:

1. Acquire EEG recordings, and, if desired, decontaminate as explained above in Section I, during three baseline conditions (step 880):
    a. During a mental performance task (i.e., reaction time, cognitive or memory task).
    b. While sitting quietly with eyes open looking straight ahead for a minimum of 5 minutes (preferably 10 minutes).
    c. While sitting quietly with eyes closed for a minimum of 5 minutes (preferably 10 minutes).
2. Compute the mean and standard deviations for each predictive variable (i.e., power of 1 Hz bins, power of EEG band, median frequency of EEG bands, etc.) for all artifact free data acquired during each of the three baseline conditions (step 880 continued).
3. Assign a Cluster Group to each baseline condition (step 880 continued).
    a. Using data from step 2., compute the Z-score for each variable by subtracting the population mean from the individual's baseline mean and dividing by the population standard deviation. The preferred model assigns membership into one of four cluster groups, so four sets of Z-scores are computed for the variables (i.e., For the 8 Hz bin during eyes open, subtract the mean for Cluster Group 1 from the power for the individual divided by the standard deviation for Cluster Group 1. Repeat this step for all Cluster Groups and variables).
    b. For each variable, compute the square of the difference between the individual's Z-score (computed in step a.) and the Cluster Z-score for each of the Cluster Groups for each baseline condition.
    c. For each Cluster Group, sum the squared differences computed in step b. across all variables for each baseline condition.
    d. Compute the square root of the result computed in step c. for each of the Cluster Groups for each baseline condition.
    e. Select the Cluster Group with the smallest (or largest, depending on the development of the cluster analysis model) value calculated in step d. as the optimal cluster group for that baseline condition.
4. Assign database membership based on the combination of Cluster Group assignments (step 890) for the Mental Performance Task ("MPT"), Eyes Open ("EO") and Eyes Closed ("EC") baseline conditions:
    a. If Cluster Group assignments are 2 or 3 for MPT; 2 for EO; and 2 or 3 for EC, then use database 1.
    b. If Cluster Group assignments are 1, 2, 3 or 4 for MPT; 3 or 4 for EO; and 3 or 4 for EOC, then use database 2.
    c. If Cluster Group assignments are 1 for MPT; 1 for EO; and 1, 2 or 3 for EC, then use database 3.

D. Adapt the Model to Individual Differences

Alternatively, or in addition to using multiple databases, the classification model can be further fitted to accommodate individual differences (step 900). The grouping of individuals into a common database helps to reduce misclassifications attributed to between-subject variability in the EEG. In order to limit the number of databases, however, subjects are grouped into the same database without having the identical Cluster Group pattern across the baseline conditions. For example, the Cluster Group assignments during the mental performance task for Database 2 range from 1 to 4 (Table 2). The procedures described below allow the classification model to be optimally fitted to the centroids derived from normative data which best fit the individual's EEG profile to minimize the potential for misclassifications.

1. Fitting the Model to the Centroids of the Assigned Database or Cluster Groups for the Three Baseline Conditions—This preferred model, described below, minimizes the potential for overfitting by deriving coefficients for the subject's baseline conditions using normative centroids. However, a large database should be acquired to ensure the centroids for each Cluster Group or database adequately represent the normative population.
    a. To develop normative centroids for each Cluster Group and/or Database:
        1) Acquire data during baseline conditions, described in II.C. 1., for the High Vigilance, Low Vigilance and Eyes Closed classes, from a large population of healthy subjects.
        2) Assign a Cluster Group for each baseline condition as described above (Step 280).
        3) Use data from a population of normative subjects, generate centroids for each Cluster Group for each Database (step 850).
    b. Then, to generate individualized coefficients for each subject:
        1) Acquire data during baseline conditions (step 880).
        2) Assign a Cluster Group, as described above, for each baseline condition (step 880 continued).
        3) Assign data base membership based on the results from step 2) (step 890)
        4) Select normative centroids which correspond to the individual's Cluster Group (and database) for each baseline condition and the Sleep class centroid from the applicable database (step 900).
        5) Apply the procedure in II.B.2 to generate coefficients for each of the predictive variables based on the centroids selected in Step 4) (step 900 continued) to implement the First-level classification model.
2. Fitting the Model to Individual Centroids for Three Baseline Conditions—This alternative approach uses the same baseline data to assign database membership for new subjects. The coefficients derived for the First-level classification model, however, are based on the individuals' centroids for each baseline condition. Since this approach uses the individual as their own control for all but the Sleepy class, it is only appropriate for testing of normal individuals or used in a test-retest model to monitor changes or improvements over time. To implement this approach:
    a. Acquire data during baseline conditions.
    b. Assign a Cluster Group, as described above, for each baseline condition.
    c. Assign data base membership based on the results from step b.
    d. Compute centroids for the three baseline conditions and select the normative centroid for the Sleepy class from the applicable database.
    e. Apply the procedures described in II.B.2. to generate individualized coefficients for each of the predictive variables based on the centroids derived in d. to implement the First-level classification model.
3. Partially Fitted Model for Three Baseline Conditions—Rather than using only the subject's baseline data or the normative data to compute the coefficients for the three baseline classes, a model can be developed that utilizes a hybrid centroid fitted to both the individual's baseline data and the normative data to generate the coefficients. To implement this approach:

a. Acquire data during baseline conditions.

b. Assign a Cluster Group, as described above, for each baseline condition.

c. Assign database membership based on the results from step b.

d. Compute the subjects' centroids for each baseline condition.

e. Selecting the normative centroid for each baseline condition and the Sleepy class for the applicable database.

f. Determine the hybrid centroids (used to determine the coefficients) based on the selected influence ("blend") of the subjects' vs. normative data.

g. Apply the procedures described in II.B.2. to generate coefficients for each of the predictive variables for the hybrid centroids for the baseline conditions and the Sleepy centroid from the applicable database to implement the First-level classification model.

E. Implementation of Multi-level Classification Model

As discussed above, classification models can be developed for multiple databases and/or adapted to overcome between-subject differences. A classification model which might be applied to quantify one-second epochs can also be implemented using either a unilevel or a multi-level approach. The inventors found that the unilevel model is adequate for providing a gross recognition of either awake or sleep. The unilevel model, however, can result in an increased number of misclassifications across individuals by class. The number of misclassifications can be reduced by deriving separate unilevel classification models for each database.

The multi-level model further improves the accuracy of the classification model by class and overcomes some of the variability attributed to individual differences observed in the unilevel model. The First-level provides an initial classification of each observation (i.e., 1-sec epoch) and the Second-level provides a more refined sub-classification. This approach, which might also be implemented as a decision tree model, has a qualitative advantage over the unilevel model. For the unilevel model, the same set of variables (i.e., power of selected EEG frequency bins, etc.) must be used for all classification decisions and the same set of coefficients must be applied to all epochs. In contrast, the multi-level model allows different sets of variables to be selected for the First- and Second-level models. Even though the same variable might be selected for two or more of the Second-level models, the coefficients for this variable may be quite different in each model. The coefficients for a given variable may also be further refined to improve classifications when First- and Second-level models are derived for separate databases.

1. First-level Classification

To begin categorizing the EEG at the first level, data is selected to train the First-level model to identify four classes. These classes were empirically selected by the inventors to provide the optimum initial classification and were used to categorize the individual's unique EEG pattern (for assignment to a database) and/or further fit the classification model to accommodate between-subject differences. The fourth class represents a Sleepy state as described in II.B.1.a.4).

A First-level output classification is assigned to each new subject/observation by applying the classification model derived from steps II.B.2.a.4) and II.B.2.a.5) with the data and coefficients obtained above in steps 870 or 900 for the initial classification model (step 910).

2. Second-level Classification

Next, the data can be classified at the Second-level, using a multiple sub-classification model (step 920). If Second-level classification is not desired, the classification results can be used for various applications (step 995). Alternatively, if further classification is desired, the following data are proposed for use in the development of the sub-classes for the second-level classification models. The same data may be used in the development of more than one sub-classification model due to the potential for misclassifications at the First-level for observations that fall between two classes. Derive sub-classification models using steps II.B.2.a with the data described below:

a. High Vigilance Sub-classification Model—derive data, preferably after initial classification as High Vigilance (output class) by the First-level classification, when subjects are:

1) Sub-Class 1—fully-rested while responding correctly to a difficult cognitive or memory task (highest alertness state).

2) Sub-class 2—fully-rested while responding correctly to a reaction-time or relatively easy cognitive or memory task.

3) Sub-class 3—fully-rested while responding incorrectly to a mental performance task.

4) Sub-class 4—fully-rested and sitting quietly with eyes open looking straight ahead.

b. Low Vigilance Sub-classification Model—derive data, preferably after initial classification as Low Vigilance (output class) by the First-level classification, when subjects are:

1) Sub-class 1—fully-rested while responding correctly to a reaction-time or relatively easy cognitive or memory task.

2) Sub-class 2—fully-rested and sitting quietly with eyes open looking straight ahead.

3) Sub-class 3—sleep deprived while responding incorrectly to a mental performance task.

4) Sub-class 4—sleep deprived and sitting quietly with eyes open looking straight ahead.

c. Sleepy Sub-classification Model—derive data, preferably after initial classification as Sleepy (output class) by the First-level classification, when subjects are:

1) Sub-class 1—sleep deprived and sitting quietly with eyes open looking straight ahead.

2) Sub-class 2—sleep deprived and sitting quietly with eyes open just prior to sleep onset.

3) Sub-class 3—sleep deprived with eyes closed.

4) Sub-class 4—sleep deprived and no longer responding to a simple behavioral task and/or sleep onset has occurred (i.e., finger-tapping).

d. Eyes Closed Sub-classification model—derive data, preferably after initial classification as Eyes Closed (output class) by the First-level classification, when subjects are:

1) Sub-class 1—fully-rested and sitting quietly with eyes closed.

2) Sub-class 2—sleep-deprived and sitting quietly with eyes closed.

3) Sub-class 3—sleep deprived with eyes closed just prior to no longer responding to a simple behavioral task (i.e., finger-tapping).

e. Previously unclassified observations are initially submitted for the First-level classification and, based on the results, submitted to the corresponding Second-level model for sub-classification.

As an alternative to the multiple sub-classification process described above, the Second-level sub-classification can be performed using a distance from the centroid method using steps II.B.2.b. The First-level classification model uses four centroids that are fitted to the individual's EEG pattern (see II.D.). To implement a sub-classification model that is also fitted to the individual, the location of the observation relative to the four centroids needs to be determined and an interpretation/classification made with respect to the observation's relative location. Since an observation can be located a given distance from the centroid in any direction, there are a number of procedures that could be employed to determine the location of the observation relative to the four centroids (e.g., vector projections, contour boundary analysis, Mahalanobis Distance analysis, etc.).

The preferred method for locating the observation would minimize the number and complexity of the calculations to enable the processing to be performed in real-time. To complete the subclassification model, regions relative to the four centroids would then need to be assigned which correspond with each sub-classification. The assignment of the regions and interpretation of observations that fall into each sub-classification region should be based on the patterns in the distribution of locations as the individual progresses from highly alert to sleep onset.

Accordingly, using the procedures described in II.B.2.b.7) above, first compute the distance: (a) between the observation and each of the three out-class centroids (i.e., classes not selected by the First-level model); and (b) between each of the out-class centroids and the in-class centroid. Note that for distance measures that utilize standard deviations in the computation, the distance between the in-class to out-class vs. out-class to in-class centroids will be different if the standard deviations of the centroids are different.

Second, compute the ratio of the distance between the observation and the out-class centroid divided by the distance between the in-class and out-class centroid for each out-class centroid. Third, determine the combinations of the ratios computed in the previous step to identify regions corresponding with each of the nominal sub-classes described in II.E.2.a., b., c., d. and e. Previously unclassified observations can then be submitted for initial First-level classification, and then submitted to the corresponding Second-level model for sub-classification.

In a currently preferred alternate embodiment, a hybrid approach to the foregoing two sub-classification approaches can be utilized. Rather than using the data previously identified as the power of the EEG for each 1 Hz bin, the EEG band and median frequencies for certain EEG bands, other variables can be used, including:

1) The distance between each of the centroids (both the in-class and the three out-class centroids) and the observation, as described above;
2) The relative distance ratio between the observation and the out-class centroid divided by the distance between the in-class and out-class centroid for each out-class centroid, as described above;
3) The distance between each centroid and the other three centroids for a total of 12 measures (i.e., distance from centroid 1 to centroid 2 not being the same as the distance from centroid 2 to centroid 1); and
4) The DFn's for the first level classification model, as described above at II.B.2.a, step 6.

Sub-classification DFA's can then be developed using these input variables instead of the data to provide the sub-classification as described for the first option.

F. Quantification of Multiple Time-sequence Observations

Multiple time-sequenced observations ("epochs") can be quantified to provide further refinement of the alertness classification along the alertness-drowsiness continuum using a real-time or off-line analysis (step 960). If this is not desired, the results of the classification analysis can be used for various applications (step 995). If the time-series analysis is to be performed, the following steps can be followed:

1. Identify sequential classifications of 3 to 10 consecutive epochs which correspond to specific physiological events:
    a. Eye blinks misclassified as Sleepy—generally one or two epochs classified as Sleepy, preceded by five or more epochs classified as High- or Low-Vigilance can be reclassified as eye blinks by implementing the following procedures:
        1) Identify epochs misclassified as Sleepy during a High or Low vigilance task that resulted from eye blinks.
        2) Determine the combination of First-level and Second-level classifications for a specified number of epochs preceding the Sleepy misclassification(s) in order to reclassify the epoch(s) as a blink.
        3) Confirm that the algorithm does not incorrectly reclassify sleepy episodes using the data described in b.1) below.
    b. Brief episodes of extreme drowsiness—one or two epochs classified as Sleepy preceded by at least one epoch classified as Eyes Closed blinks by implementing the following procedures:
        1) Select epochs classified as Eyes Closed or Sleepy from subjects who are sleep deprived and performing a task that requires the eyes open.
        2) Determining the combination of time-sequenced First-level classifications to accurately identify these drowsy episodes.
        3) Confirming the algorithm does not incorrectly classify eye blinks as drowsy episodes using the data described in a. 1) above.
2. Time-Series Analysis to Predict Performance Deterioration—Utilize the information provided by the classification model for each epoch from the most recent period (i.e., 10 to 15-seconds) as well as summary information from the past (i.e., 1-minute to 2-hours) to predict performance under specific conditions. For example, subjects with sleep deprivation exhibiting a level of vigilance that results in poor performance during a mental performance task requiring high vigilance but performing adequately during a task that requires a sustained level of low vigilance (driving). The following procedure can be implemented:
    a. Select input variables to the Time-series analysis. The variables described below provide the best resolution from the classification output (as opposed to only using the nominal output class):
        1) The DFn's for all four classes from the First-level classification model for a set of time-sequenced epochs (i.e., most recent 10-seconds).
        2) Either the DFn's for the sub-classes (see II.B.2.a and II.E.2.) or the four distance measurements (see II.B.2.b. and II.E.2.), depending upon the method selected, for a set of time-sequenced epochs (i.e., most recent 10-seconds).

3) Summary results from the classification model over a wider time window:
    a) number of episodes identified by step II.F. 1.b. for a given period (i.e., previous 1-minute, 5-minutes, 15-minutes, 1-hour, etc.)
    b) number of First- and Second-level classifications by class for a given period (i.e., number of High Vigilance, Low Vigilance, Eyes Closed and Sleepy classes during previous 1-minute, 5 minutes, 15-minutes, 1-hour, etc.).
  b. Assign a single input class to each epoch. The input class can be derived from one or several of the data described below that would be useful in categorizing the subject's state:
    1) Number of hours the subject has been awake.
    2) Subject's perceived level of sleepiness, happiness, stress, ability to concentrate, level of attention or level of cognition.
    3) Performance measurements during activities that require a high level of vigilance or a minimal level of sustained vigilance. Alternative tasks could be used to generate the performance measured. Several types of task characteristics can be utilized in this regard:
      a) High Vigilance, Mental Performance—the occurrence of a stimulus-response event, response time, correct vs. incorrect response, or relative difficulty of the stimulus during a mental performance (high vigilance) task.
      b) Sustained Vigilance—based on actual speed, distance from center of lane, drifting vs. steering from the center of the lane, presentation of a divided attention task, difficulty of driving scenario, occurrence of accidents or physiological indices of drowsiness (visual inspection of video indicating the subject was having difficulty remaining awake) while operating a driving simulator.
  c. Developing a classification model described in step II.B.2. above to utilize the input variables from step II.F.2.a. to classify the categories derived in step II.F.2.b.

III. Applications for the Classification System

Returning now to FIG. 1B, the results of the classification system described above can be implemented for various applications in real-time using a digital signal processing chip or off-line using a standard micro-processor based computer (step 170). The preferred hardware configuration includes impedance checking circuitry that is initiated when the electrodes are applied and then, routinely or on demand, measures the scalp-electrode impedance (measured in $K\Omega$). Alternatively, the impedance checking can be initiated based on the identification of 60 Hz interference (see section I.B). Software then compares the scalp-electrode impedance value to a pre-established threshold (e.g., optimally below 5 $k\Omega$) and notifies the user via a visual (e.g., LCD display) and/or audio (e.g., speech chip) alarm (preferably using a LCD display and/or a speech chip to generate a verbal message) to identify the electrode that requires attention.

For off-line applications, the preferred hardware configuration includes an A/D converter to digitize the data, a sufficient data storage capacity (e.g., flash memory chips, PCMCIA card or a hard disk) and minimal user requirements to download data during the recording period. For the preferred configuration (i.e., sampling rate at 256 samples/sec acquired from channels CzPz and CzOz), approximately 3.7 MB of data storage is required per hour of recording time. The typical recording period for off-line applications described below is approximately 8 hours.

For real-time applications, and A/D converter is required to digitize the data and a digital signal processing chip is required to process the rules described in sections I and II above. A minimal amount of data storage capacity is required to: (a) acquire the baseline data necessary to assign a database and fit the classification model, (b) store the input data to the time-series analysis, and (c) save information that could be used to generate a summary report with respect to the user's overall vigilance during a period of use. This configuration requires approximately 8 MB of flash memory. A speech or audio chip is required so that the user can be warned when a pre-selected threshold level of alertness is identified (i.e., sleep onset imminent).

Specifically, the following applications can be implemented:

A. Real-time Monitoring and Feedback Based on Adult Normative Indices

For the preferred configuration, the methods described previously (i.e., First-and Second-level classification model plus the time-series analysis) are used to monitor an individual and classify an individual's EEG along the alertness-drowsiness continuum. The following can be monitored:

1. Alertness—Certain jobs require an individual to maintain a relatively high state of alertness for a short period. If a high level of alertness is not achieved or maintained, an accident might result (e.g., pilot landing an airplane). For other jobs, an elevated state of alertness must be maintained for extended periods even when the task is relatively monotonous (e.g., air traffic controller monitoring a radar screen). For either of these applications, the classification system can be used to ensure the appropriate level of alertness is maintained. Warning alarms can be initiated, based on, but not limited to:
   a. The number of the First-level classes over a short time interval (e.g., 5-minutes) are skewed toward Low Vigilance compared to an equal distribution between Low and High Vigilance.
   b. The number of drowsy episodes in a given time interval (e.g., 15-minutes)
   c. The number of epochs classified as Eyes Closed during a given time interval (e.g., 15-minutes).
   d. Results from the time series analysis indicates performance errors could occur during a mental performance task.

2. Drowsiness—shift workers (e.g., swing or graveyard shifts) exhibit greater sleepiness on-the-job compared to workers who perform the same task during daytime hours, in part, because many shift workers report difficulty sleeping during daytime hours and they are required work during the hours of maximum sleepiness. Many workers who are truck drivers, train operators, or airline pilots are vulnerable to sleepiness because they work through the night, in many cases unaccompanied, and obtain less than 6 hours of sleep per day at irregular intervals. Circadian rhythms also influence sleepiness, helping to explain why approximately 54% of motor vehicle accidents occur at night and during the maximum sleepiness hours between 2 AM to 7 AM and 2 PM to 5 PM. Individuals who suffer from sleep disorders are prone to both daytime and night time fatigue. The results of the method of the present invention can be used to assist in the management of fatigue by ensuring users are warned not only when sleep onset is imminent but also in advance so effective fatigue countermeasures can be employed. The decision as to which classification rule(s) should be employed depends on the user's selection with respect to identifying the optimum time for a strategic nap (which will result in a greater number of warnings) vs. notification at the onset of sleep.

a. To notify the use prior to the onset of sleep, the criteria could be based on, but not limited to:
  1) A predetermined number of epochs classified as Eyes Closed or Sleepy by the First- or Second-level classification model.
  2) Every drowsy episode of a minimal length (e.g., five seconds) as determined by the time-series analysis described above.
  3) When two or more brief drowsy episodes determined by the time-series analysis occur in a 1-minute period.
  4) Results of the time series analysis indicating performance errors could occur during a minimally challenging sustained vigilance task.
b. To notify the user when a strategic nap should be taken to improve their capability to sustain vigilance, the criteria could be based on, but not limited to:
  1) The number of the Second-level classes over a short time interval (e.g., 5 minutes) that falls into a range indicating a very sleep deprived state.
  2) The number of drowsy episodes over a number of time intervals (e.g., most recent 15 minutes and 60 minutes).
  3) Results of the time series indicating performance errors could occur during a mental performance task to indicate an initial level of fatigue.
  4) Results of the time series indicating performance errors could occur during a minimally challenging sustained vigilance task to indicate the user has become increasingly fatigued compared to 3).
c. To predict how quickly the user may reach sleep onset, criteria could be based on, but not limited to:
  1) The amount of time elapsed between the identification of abnormally low sustained vigilance and the initial indication that a strategic nap would be beneficial.
  2) The amount of time that elapsed between the identification of potential performance errors during mental performance tasks and a sustained low vigilance task.
  3) The combination of 1) and 2) above.

B. Real-Time Monitoring and Feedback for Patients with Attention Deficit and Sleep Disorders Attention Deficit Disorder and Attention Deficit/Hyperactivity Disorder (ADHD), although primarily diagnosed in male children, is estimated to affect 7–12% of the population. A popular theory of the etiology of ADHD explains the symptom such as inattention, disorganization, distractibility, impulsiveness, and excessive motor activity as a result of a state of decreased arousal that leads to a constant search for stimulation. Researchers have shown that the brainwave patterns of ADHD patients during periods of decreased arousal are similar to the brainwave patterns of normal individuals exhibiting extremely low vigilance (i.e., sleepy). One therapy for ADHD is neurofeedback, a form of biofeedback designed to enhance and/or decrease specific frequency bands of electrical activity recorded from the brain. Recent studies suggest that children with reading disorders and slow learners have similar brain wave characteristics as ADHD patients and may also benefit from neurofeedback training.

The results of the classification method of the present invention can be applied directly to provide neurofeedback training to adults since normative data was used to develop the models. The classification models can be adapted to provide neurofeedback training to children by first acquiring a normative database for the age specific group during high and low vigilance tasks. The procedures described previously are then applied to: group individuals' databases, implement the First- and Second-level models, further fit the model for individual differences, and develop the time-series analysis. Data acquired from patients with ADHD in a state of low arousal are then substituted for the data acquired from sleep deprived subjects for the input class previously described as Sleepy. Warning alarms for the ADHD model are based on criteria similar to those described in II.B.2., II.E.2, and II.F. to identify low states of alertness or a combination of criteria described in III.A.1. and III.A.2. above.

C. Recording EEG Data for Subsequent Off-line Analysis

The results of the method of the present invention can be used to analyze data previously recorded to assess the individual's level of alertness during a specified task (e.g., during a mental performance task) or during an unspecified range of tasks that might be encountered during activities of daily living. The results of the method of the present invention can be used to provide an objective measure of alertness for the following applications:

1. Pharmacological Monitoring—It is common for individuals diagnosed with narcolepsy or attention deficit/hyperactivity disorder to be treated with stimulants, however, there is presently no objective measure available to assess and optimize (i.e., titrate) the dosage. Because the classification system is based on normative data, the following procedures are used to titrate the dosage:
  a. Compare the number of epochs classified into each of the First-and Second-level classes during mental performance tasks to a normal group.
  b. Compare the number of epochs classified into each of the First- and Second-level classes over the course of an 8-hour period vs. a population of normal subjects performing a variety of tasks corresponding to activities of daily living (e.g., watching a movie, reading, working on a computer, etc.).

2. To evaluate patients with sleep disorders, the following procedures are used:
  a. A Maintenance of Wakefulness Test (MWT) is a procedure commonly used in sleep medicine to assess daytime drowsiness for subjects with sleep disorders. Patients sit in a semi-reclined chair in a darkly lit room and try to remain awake for 40 minutes. This procedure is repeated every 2-hours between the hours of 8 AM and 4 PM. The MWT is terminated when the subject has been asleep for 90 continuous seconds. The MWT has been used to evaluate individuals who report symptoms typical of patients with sleep disorders to assist with the diagnosis. Alternatively, the MWT has been used to assess improved states of alertness after the patient has received treatment for their sleep disorder. The results of the method of the present invention can provide a more refined assessment of the subject's state during a MWT as compared to simply waiting for the individual to fall asleep. This refined analysis, when compared to normal subjects, will allow fewer MWT's to be performed in order to screen subjects for excessive daytime drowsiness and monitor treatment outcomes for sleep disorder patients.
  b. Assessing Excessive Daytime Sleepiness—EEG recordings can be acquired during an 8-hour period while the user performs their regular activities of daily living. An analysis of the data using the procedures described in III.B.1. and III.B.2. can be used to assess the user's relative level of vigilance compared to a population of normal subjects performing a variety of tasks corresponding to activities of daily living (e.g., watching a movie, reading, working on a computer, etc.).

3. Assessing Improvements in the Level of Sustained Alertness.
   a. The effects from repeated neurofeedback training sessions can be assessed using summary data derived during each neurofeedback training session. For example, the number and duration of periods with abnormal levels of attention could be saved for each training session and compared across sessions to identify significant improvements in the user's ability to sustain higher levels of alertness.

Thus, a method has been disclosed for monitoring EEG activity and classifying the data accurately into states of alertness. It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A method for locating eye-blinks in the electroencephalogram (EEG) without the use of concurrent electroocculogram (EOG) signals, comprising the steps of:

acquiring EEG signals of a person from a plurality of EEG electrode sites for a plurality of sequential epochs;

determining a plurality of cross-correlation variables from the EEG signals;

extracting at least one output variable from said plurality of cross-correlation variables determined to be predictive in identifying eye-blinks in the EEG signals; and locating the eye-blinks within corresponding epochs in the EEG signal based upon said at least one output variable.

2. The method of claim 1, further comprising generating said thresholds based upon one of a discriminant function, neural network and a non-linear analysis technique.

3. The method of claim 1, further comprising generating said output variables a cross-correlation analysis.

4. The method of claim 1, further comprising the identification and location of eye-blinks in the EEG signals in real-time.

5. The method of claim 1, wherein said plurality of cross-correlation variables are cross-covariance variables.

6. The method of claim 1, further comprising determining said predictive variables based upon a database of EEG signal data acquired from a plurality of subjects.

7. The method of claim 1, further comprising determining said thresholds based upon a database of EEG signal data acquired from a plurality of subjects.

8. The method of claim 1, further comprising identifying eye blinks in the EEG signals based upon variables derived from a Fast Fourier transform as additional threshold inputs.

9. A method for determining a system for identifying eye blinks in the electroencephalogram (EEG) which utilizes only the EEG signal for identification of the eye blinks, comprising the steps of:

acquiring EEG and electroocculogram (EOG) signals of a person from a plurality of EEG and EOG electrode sites for a plurality of sequential epochs which contain eye-blinks;

determining a plurality of cross-correlation variables from the EEG signals and generating output variables based upon the plurality of cross-correlation variables;

utilizing an EOG channel to confirm the presence of an eye-blink in the EEG signals;

establishing thresholds for said output variables to identify the presence of eye-blinks in the EEG signals.

10. The method of claim 9, further comprising determining said thresholds based upon EEG signal data which contain eye-blinks and with theta waves.

11. The method of claim 9, further comprising determining said thresholds based upon a database of EEG signal data acquired from a plurality of subjects.

12. The method of claim 9, further comprising identifying eye blinks based upon one of a discriminant function, neural network and a non-linear analysis technique which utilizes said output variables.

13. The method of claim 9, wherein said plurality of cross-correlation variables are cross-covariance variables.

* * * * *

UNITED STATES PATENT AND TRADEMARK OFFICE
CERTIFICATE OF CORRECTION

PATENT NO.         : 6,625,485 B2
APPLICATION NO.    : 10/172060
DATED              : September 23, 2003
INVENTOR(S)        : Daniel J. Levendowski et al.

It is certified that error appears in the above-identified patent and that said Letters Patent is hereby corrected as shown below:

Column 1, lines 10-14, delete "The United States Government has rights to this invention pursuant to research supported in whole or in part by NIH contracts R43NS6344 and N43NS72367 and grant R43NS35387 awarded by the National Institute of Neurological Disease and Stroke." and insert instead --This invention was made with government support under NIH contracts N43NS62344 and N43NS72367 and grant R43NS35387 awarded by the National Institute of Neurological Disorders and Stroke. The government has certain rights in the invention.--

Signed and Sealed this

Twenty-ninth Day of June, 2010

David J. Kappos
*Director of the United States Patent and Trademark Office*